United States Patent
Pajouhesh et al.

(10) Patent No.: US 8,629,149 B2
(45) Date of Patent: Jan. 14, 2014

(54) OXOPIPERAZINE DERIVATIVES FOR THE TREATMENT OF PAIN AND EPILEPSY

(75) Inventors: Hassan Pajouhesh, West Vancouver (CA); Yanbing Ding, Richmond (CA)

(73) Assignee: Zalicus Pharmaceuticals Ltd., Vancouver (CA)

( * ) Notice: Subject to any disclaimer, the term of this patent is extended or adjusted under 35 U.S.C. 154(b) by 0 days.

(21) Appl. No.: 13/393,374

(22) PCT Filed: Sep. 3, 2010

(86) PCT No.: PCT/CA2010/001385
§ 371 (c)(1),
(2), (4) Date: May 17, 2012

(87) PCT Pub. No.: WO2011/026240
PCT Pub. Date: Mar. 10, 2011

(65) Prior Publication Data
US 2012/0220605 A1   Aug. 30, 2012

Related U.S. Application Data

(60) Provisional application No. 61/239,931, filed on Sep. 4, 2009.

(51) Int. Cl.
*A61K 31/495* (2006.01)
*C07D 241/08* (2006.01)

(52) U.S. Cl.
USPC .................. 514/255.01; 544/384

(58) Field of Classification Search
USPC .................. 544/391; 514/255.01
See application file for complete search history.

(56) References Cited

U.S. PATENT DOCUMENTS

| | | | |
|---|---|---|---|
| 6,011,035 A | 1/2000 | Snutch et al. | |
| 6,294,533 B1 | 9/2001 | Snutch et al. | |
| 6,387,897 B1 | 5/2002 | Snutch | |
| 6,492,553 B1 * | 12/2002 | Hulme et al. | 564/129 |
| 6,617,322 B2 | 9/2003 | Snutch | |
| 6,951,862 B2 | 10/2005 | Snutch et al. | |
| 2004/0044004 A1 | 3/2004 | Snutch et al. | |
| 2004/0259866 A1 | 12/2004 | Snutch et al. | |
| 2004/0266784 A1 | 12/2004 | Snutch et al. | |
| 2006/0084660 A1 | 4/2006 | Snutch et al. | |

FOREIGN PATENT DOCUMENTS

| | | |
|---|---|---|
| CA | 2318601 A1 | 8/1999 |
| WO | WO-01/10799 A1 | 2/2001 |

OTHER PUBLICATIONS

Arimoto et al., "Semisynthetic β-lactam antibiotics. III. Synthesis and antibacterial activity of 7β-[2-(2-aminothiazol-4-yl)-2-(substituted carbamoylmethoxyimino)acetamido]cephalosporins," *J Antibiot* (Tokyo). 39(9):1243-1256, 1986.
Hulme et al., "Novel safety-catch linker and its application with a Ugi/De-BOC/Cyclization (UDC) strategy to access carboxylic acids, 1,4-benzodiazepines, diketopiperazines, ketopiperazines and dihydroquinoxalinones," *Tetrahedron Letters* 39(40):7227-7230, 1998.
Hulme et al., "Applications of N-BOC-diamines for the solution phase synthesis of ketopiperazine libraries utilizing a Ugi/De-BOC/Cyclization (UDC) strategy," *Tetrahedron Letters* 39(44):8047-8050, 1998.
Hulme et al., "Novel applications of ethyl glyoxalate with the Ugi MCR," *Tetrahedron Letters* 40(29):5295-5299, 1999.
Hulme et al., "Novel applications of resin bound α-amino acids for the synthesis of benzodiazepines (via Wang resin) and ketopiperazines (via hydroxymethyl resin)," *Tetrahedron Letters* 41(10):1509-1514, 2000.
International Search Report for International Patent Application No. PCT/CA/2010/001385, mailed Dec. 7, 2010 (16 pages).
International Preliminary Report on Patentability issued in International Application No. PCT/CA2010/001385, issued Mar. 6, 2012.
Written Opinion of the International Searching Authority for International Application No. PCT/CA2010/001385, mailed Dec. 7, 2010 (7 pages).

* cited by examiner

*Primary Examiner* — Yong Chu
*Assistant Examiner* — Karen Cheng
(74) *Attorney, Agent, or Firm* — Clark & Elbing LLP

(57) ABSTRACT

Compounds of formula (I) which are useful in ameliorating conditions characterized by unwanted sodium and/or calcium channel actrvrh, particularly Na$_v$ 1, 7, Na$_v$ 1, 8, or Ca$_v$ 3, 2 channel activity are disclosed. More specifically, compounds for use in the treatment of conditions such as epilepsy, cancer, pain, migraine, Parkinson's disease, depression, schizophrenia, psychosis, and tinnitus are disclosed.

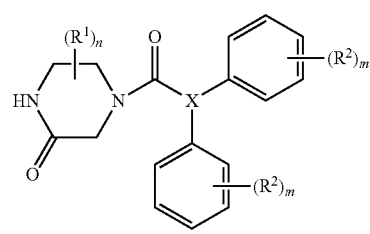

22 Claims, 1 Drawing Sheet

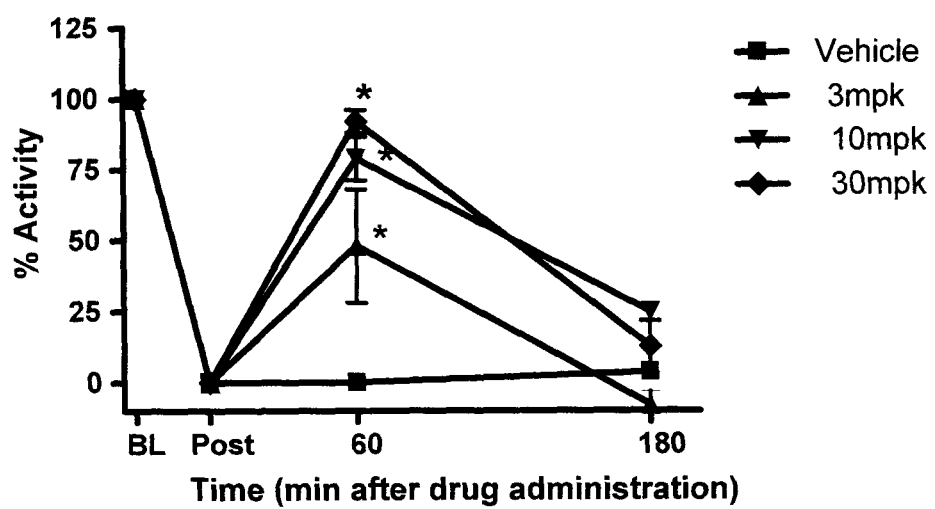

OXOPIPERAZINE DERIVATIVES FOR THE TREATMENT OF PAIN AND EPILEPSY

CROSS-REFERENCE TO RELATED APPLICATIONS

This application is the U.S National Stage Application of PCT/CA2010/001385, which claims benefit of U.S. Provisional Application No. 61/239,931, filed Sep. 4, 2009, each of which is hereby incorporated by reference.

FIELD OF THE INVENTION

The invention relates to compounds useful in treating conditions associated with calcium channel function, and particularly conditions associated with sodium channel and T-type calcium channel activity. More specifically, the invention concerns compounds containing piperazine-N-arylacetamide and piperazine-aryl-isoxazole derivatives that are useful in treatment of conditions such as epilepsy, cancer, pain, migraine, Parkinson's Disease, depression, schizophrenia, psychosis, and tinnitus.

BACKGROUND OF THE INVENTION

Voltage-gated sodium ($Na_v$) channels are present in neurons and excitable tissues where they contribute to processes such as membrane excitability and muscle contraction (Ogata et al., *Jpn. J. Pharmacol.* (2002) 88(4) 365-77). Nine different transmembrane α-subunits ($Na_v$1.1-1.9) from a single $Na_v$1 family combine with auxiliary β-subunits that modify channel function to form functional $Na_v$ channels. Of the nine $Na_v$1 α-subunit isoforms, five are expressed in the dorsal root ganglion where they are involved in setting the resting membrane potential and the threshold for generating action potentials, and also contribute to the upstroke as well as firing of action potentials during sustained depolarization. In particular, the tetrodotoxin (TTX) sensitive $Na_v$1.7 and TTX-insensitive $Na_v$1.8 channel subtypes act as major contributors to both inflammatory and neuropathic pain (Momin et al., *Curr Opin Neurobiol.* 18(4):383-8, 2008; Rush et al., *J Physiol.* 579(Pt 1):1-14, 2007).

Calcium channels mediate a variety of normal physiological functions and are also implicated in a number of human disorders. Examples of calcium-mediated human disorders include but are not limited to congenital migraine, cerebellar ataxia, angina, epilepsy, hypertension, ischemia, and some arrhythmias (see, e.g., Janis et al., *Ion Calcium Channels: Their Properties, Functions, Regulation and Clinical Relevance* (1991) CRC Press, London). T-type, or low voltage-activated, channels describe a broad class of molecules that transiently activate at negative potentials and are highly sensitive to changes in resting potential and are involved in various medical conditions. For example, in mice lacking the gene expressing the 3.1 subunit, resistance to absence seizures was observed (Kim et al., *Mol Cell Neurosci* 18(2): 235-245, 2001). Other studies have also implicated the 3.2 subunit in the development of epilepsy (Su et al., *J Neurosci* 22: 3645-3655, 2002).

Novel allosteric modulators of the slow-inactivation sodium or the slow-inactivation calcium channel are thus desired. Modulators may affect the kinetics and/or the voltage potentials of the slow-inactivation of one or any combination of $Na_v$1.7, $Na_v$1.8 or $Ca_v$3.2 channels.

SUMMARY OF THE INVENTION

The invention relates to heterocyclic compounds useful in conditions modulated by sodium and/or calcium channels. The compounds of the invention are oxopiperazine derivatives.

In one aspect, the invention relates to a compound of the formula:

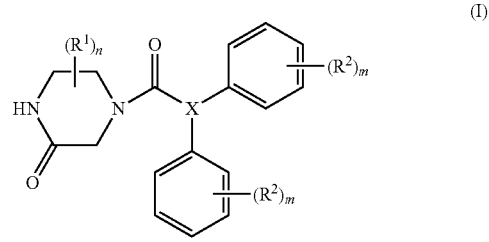

or a pharmaceutically acceptable salt, solvate, or prodrug thereof, or a stereoisomer thereof, or a conjugate thereof, where X is an optionally substituted alkylene (1-6C), alkenylene (2-6C), alkynylene (2-6C), heteroalkylene (2-6C), heteroalkenylene (2-6C), or heteroalkynylene (2-6C);

n is an integer between 0-6;

each m is, independently, an integer between 0-5;

wherein when n is 0 and X is $CH_2CH_2$, at least one m is not 0;

wherein when n is 1, each m is 0, and X is $CH_2$, $R^1$ is not $(CH_2)C_6H_5$, $(CH_2)_2C_6H_5$, or CONHR', where R' is optionally substituted alkyl (1-6C) or optionally substituted aryl;

each $R^1$ is, independently, selected from halo, CN, $NO_2$, $CF_3$, $OCF_3$, COOR', CONR'$_2$, OR', SR', SOR', $SO_2$R', NR'$_2$, NR'(CO)R', and NR'$SO_2$R', wherein each R' is independently H or an optionally substituted group selected from alkyl, alkenyl (2-6C), alkynyl (2-6C), heteroalkyl (2-6C) heteroalkenyl (2-6), and heteroalkynyl (2-6C); or each R' is selected from optionally substituted alkyl (1-6C), optionally substituted alkenyl (2-6C), optionally substituted alkynyl (2-6C), heteroalkyl (2-6C), optionally substituted heteroalkenyl (2-6C), optionally substituted heteroalkynyl (2-6C), =O, or =NOR'; and each $R^2$ is, independently, selected from halo, CN, $NO_2$, $CF_3$, $OCF_3$, COOR', CONR'$_2$, OR', SR', SOR', $SO_2$R', NR'$_2$, NR'(CO)R', and NR'$SO_2$R', wherein each R' is independently H or an optionally substituted group selected from alkyl (1-6C), alkenyl (2-6C), alkynyl (2-6C), heteroalkyl (2-6C) heteroalkenyl (2-6), and heteroalkynyl (2-6C); or each $R^2$ is an optionally substituted group selected from alkyl (1-6C), alkenyl (2-6C), alkynyl (2-6C), heteroalkyl (2-6C), heteroalkenyl (2-6C), or heteroalkynyl (2-6C).

In some embodiments, each R' is, independently, selected from halo, CN, $NO_2$, $CF_3$, $OCF_3$, COOR', OR', SR', SOR', $SO_2$R', NR'$_2$, NR'(CO)R', and NR'$SO_2$R', wherein each R' is independently H or an optionally substituted group selected from alkyl (1-6C), alkenyl (2-6C), alkynyl (2-6C), heteroalkyl (2-6C) heteroalkenyl (2-6), and heteroalkynyl (2-6C); or each R' is selected from unsubstituted alkyl (1-6C), optionally substituted alkenyl (2-6C), optionally substituted alkynyl (2-6C), heteroalkyl (2-6C), optionally substituted heteroalkenyl (2-6C), optionally substituted heteroalkynyl (2-6C), =O, or =NOR'.

In some embodiments, the phenyl rings are both on one carbon of X, which may be the terminal carbon of X.

In other embodiments, X is an optionally substituted alkylene (1-6C), alkenylene (2-6C) or heteroalkylene (2-6C). In certain embodiments, X is $(CH_2)_{0-4}CH=C$, or $(CH_2)_{0-4}(Y)_{0-1}CH$ where Y is NH, S, or SO. In further embodiments, X is CH, $CH_2CH$, $(CH_2)_4CH$, $CH=C$, NHCH. or $CH_2S(O)CH$.

In still other embodiments, n is 0-2. In certain embodiments, n is 0.

In some embodiments, each $R^1$ is methyl, and n is 1 or 2.

In other embodiments, each $R^2$ is independently halo or methyl.

In certain embodiments, each m is independently 0-2. In further embodiments, each m is independently 0 or 1.

In some embodiments, the compound has a structure according to

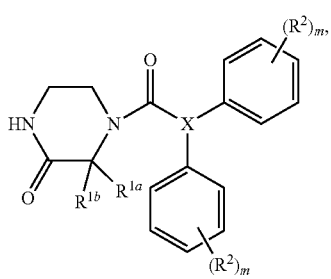

(II)

where each $R^{1a}$ and $R^{1b}$ is selected, independently, from H or unsubstituted 1C-6C alkyl; X is CH, $CH_2CH$, $(CH_2)_{2-4}CH$?, $CH=C$, NHCH, or $CH_2S(=O)CH$; each m is, independently, 0, 1, or 2; and each $R^2$ is, independently, optionally substituted 1C-6C alkyl or halogen. In further embodiments, both $R^{1a}$ and $R^{1b}$ are unsubstituted 1C-6C alkyl (e.g., both $R^{1a}$ and $R^{1b}$ are methyl). In other embodiments, both $R^{1a}$ and $R^{1b}$ are H. In still other embodiments, $R^{1a}$ is H and $R^{1b}$ is unsubstituted 1C-6C alkyl (e.g., methyl). In some embodiments, the carbon to which $R^{1a}$ and $R^{1b}$ are bonded has the R configuration. In other embodiments, the carbon to which $R^{1a}$ and $R^{1b}$ are bonded has the S configuration. In certain embodiments, each m is 0 or 1. In other embodiments, each m is 1. In some embodiments, both $R^2$ are ortho, meta, or para to X. In still other embodiments, each $R^2$ is selected, independently, from fluoro, chloro, or unsubstituted 1C-6C alkyl (e.g., methyl). In certain embodiments, all $R^2$ groups are fluoro, or all $R^2$ groups are chloro, or all $R^2$ groups are methyl.

In some embodiments, the compound is selected from the compounds of Table 1.

TABLE 1

| Compound No. | Name | Structure |
|---|---|---|
| 1 | N-benzhydryl-3-oxopiperazine-1-carboxamide | 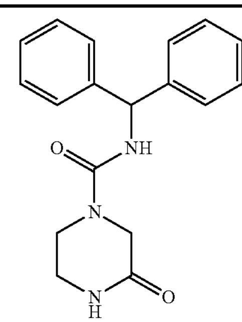 |
| 2 | 4-(2-(benzhydrylsulfinyl)acetyl)piperazin-2-one | 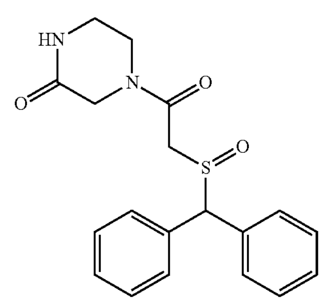 [SMILES: O=C1CN(C(=O)CS(=O)C(c2ccccc2)c2ccccc2)CCN1] |
| 3 | 4-(3,3-bis(4-chlorophenyl)propanoyl)piperazin-2-one | 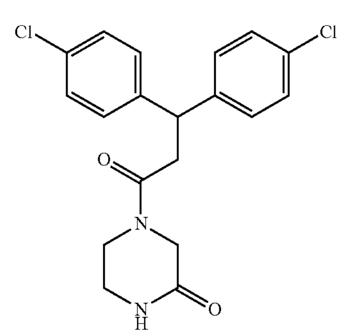 [SMILES: O=C1CN(C(=O)CC(c2ccc(Cl)cc2)c2ccc(Cl)cc2)CCN1] |

TABLE 1-continued

| Compound No. | Name | Structure |
|---|---|---|
| 5 | 4-(3,3-di-tolylpropanoyl)piperazin-2-one | 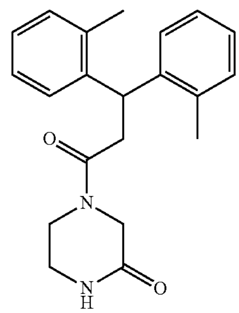 [SMILES: Cc1ccccc1C(CC(=O)N1CCNC(=O)C1)c1ccccc1C] |
| 6 | 4-(6,6-diphenylhexanoyl)piperazin-2-one | 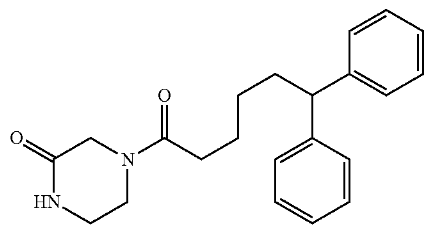 [SMILES: O=C1CN(C(=O)CCCCC(c2ccccc2)c2ccccc2)CCN1] |
| 7 | 4-(2,2-diphenylacetyl)piperazin-2-one | 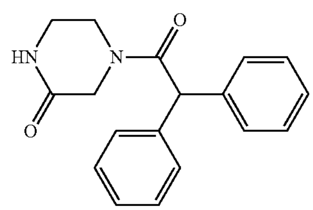 [SMILES: O=C1CN(C(=O)C(c2ccccc2)c2ccccc2)CCN1] |
| 8 | 4-(3,3-diphenylacryloyl)piperazin-2-one | 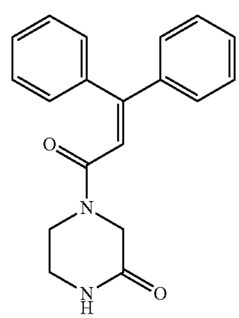 [SMILES: O=C1CN(C(=O)C=C(c2ccccc2)c2ccccc2)CCN1] |
| 9 | 4-(3,3-bis(4-fluorophenyl)propanoyl)piperazin-2-one | 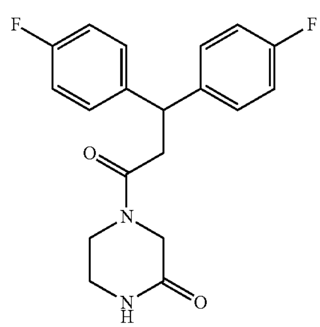 [SMILES: O=C1CN(C(=O)CC(c2ccc(F)cc2)c2ccc(F)cc2)CCN1] |

TABLE 1-continued

| Compound No. | Name | Structure |
|---|---|---|
| 10 | 4-(3,3-diphenylpropanoyl)-3,3-dimethylpiperazin-2-one | 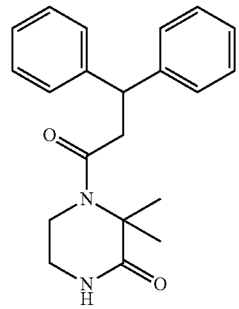 [SMILES: CC1(C)C(=O)NCCN1C(=O)CC(c1ccccc1)c1ccccc1] |
| 11 | (R)-4-(3,3-diphenylpropanoyl)-3-methylpiperazin-2-one | 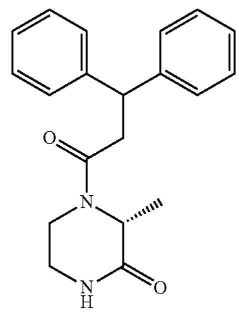 [SMILES: C[C@@H]1C(=O)NCCN1C(=O)CC(c1ccccc1)c1ccccc1] |
| 12 | (S)-4-(3,3-diphenylpropanoyl)-3-methylpiperazin-2-one | 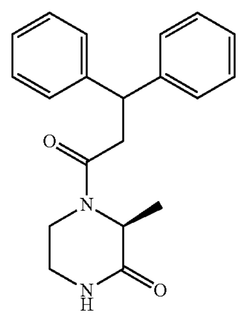 [SMILES: C[C@H]1C(=O)NCCN1C(=O)CC(c1ccccc1)c1ccccc1] |
| 13 | 4-(2,2-bis(4-chlorophenyl)acetyl)piperazin-2-one | 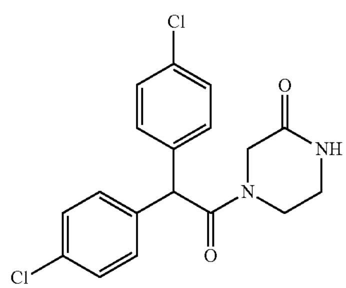 [SMILES: O=C1CN(C(=O)C(c2ccc(Cl)cc2)c2ccc(Cl)cc2)CCN1] |
| 14 | 4-(2-(diphenylamino)acetyl)piperazin-2-one | 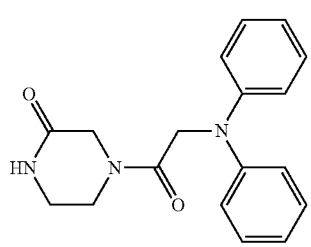 [SMILES: O=C1CN(C(=O)CN(c2ccccc2)c2ccccc2)CCN1] |

TABLE 1-continued

| Compound No. | Name | Structure |
|---|---|---|
| 15 | 4-(3,3-bis(4-fluorophenyl)propanoyl)-3,3-dimethylpiperazin-2-one | 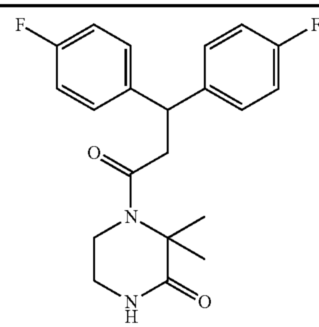 |

In further embodiments, the compound is

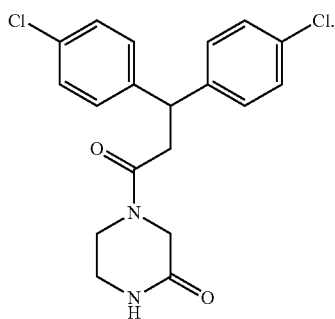

In another aspect, the invention relates to a pharmaceutical composition that includes a pharmaceutically acceptable excipient and
(a) any of the compounds described herein (e.g. a compound according to Formula (I) or (II), or any of Compounds 1-3 and 5-15); or
(b) a compound according to formula (III),

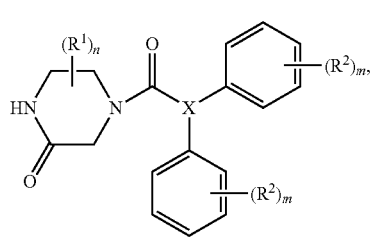

or a pharmaceutically acceptable salt, solvate, or prodrug thereof, or a stereoisomer thereof, or a conjugate thereof, where
X is an optionally substituted alkylene (1-6C), alkenylene (2-6C), alkynylene (2-6C), heteroalkylene (2-6C), heteroalkenylene (2-6C), or heteroalkynylene (2-6C);
n is an integer between 0-6;
each m is, independently, an integer between 0-5;
each $R^1$ and $R^2$ is independently selected from halo, CN, $NO_2$, $CF_3$, $OCF_3$, COOR', CONR'$_2$, OR', SR', SOR', $SO_2$R', NR'$_2$, NR'(CO)R', and NR'$SO_2$R', wherein each R' is independently H or an optionally substituted group selected from alkyl (1-6C), alkenyl (2-6C), alkynyl (2-6C), heteroalkyl (2-6C) heteroalkenyl (2-6), and heteroalkynyl (2-6C); or the optional substituents may be one or more optionally substituted groups selected from alkyl (1-6C), alkenyl (2-6C), alkynyl (2-6C), heteroalkyl (2-6C), heteroalkenyl (2-6C), or heteroalkynyl (2-6C); and wherein each $R^1$ may further be selected from =O and =NOR'.

In some embodiments, the pharmaceutical composition is formulated in unit dosage form. In further embodiments, the unit dosage form is a tablet, caplet, capsule, lozenge, film, strip, gelcap, or syrup.

The invention is also directed to the use of a compound described herein (e.g., a compound according to any of Formulas (I)-(III) or any of compounds 1-15) for the preparation of medicaments for the treatment of conditions (e.g., conditions requiring modulation of sodium and/or calcium channel activity (e.g., $Na_v$ 1.7, $Na_v$ 1.8, and $Ca_v$ 3.2 channel activity, or any combination thereof of sodium and calcium channels)).

In another aspect, the invention features a method to treat a condition (e.g., pain or epilepsy), where the method includes administering to a subject in need of such treatment an amount (e.g., an effective amount) of
(a) any of the compounds described herein (e.g. a compound according to Formula (I) or (II), or any of Compounds 1-3 and 5-13); or
(b) a compound according to formula (III),

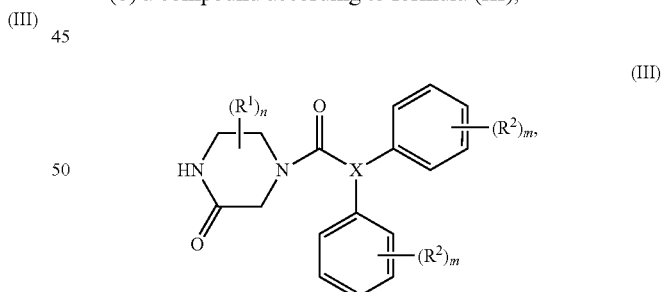

or a pharmaceutically acceptable salt, solvate, or prodrug thereof, or a stereoisomer thereof, or a conjugate thereof, where
X is an optionally substituted alkylene (1-6C), alkenylene (2-6C), alkynylene (2-6C), heteroalkylene (2-6C), heteroalkenylene (2-6C), or heteroalkynylene (2-6C);
n is an integer between 0-6;
each m is, independently, an integer between 0-5;
each $R^1$ and $R^2$ is independently selected from halo, CN, $NO_2$, $CF_3$, $OCF_3$, COOR', CONR'$_2$, OR', SR', SOR', $SO_2$R', NR'$_2$, NR'(CO)R', and NR'$SO_2$R', wherein each R' is independently H or an optionally substituted group selected from alkyl (1-6C), alkenyl (2-6C), alkynyl (2-6C), heteroalkyl (2-6C) heteroalkenyl (2-6), and heteroalkynyl (2-6C); or the optional substituents may be one or more optionally substituted groups selected from alkyl (1-6C), alkenyl (2-6C), alkynyl (2-6C), heteroalkyl (2-6C), heteroalkenyl (2-6C), or heteroalkynyl (2-6C); and wherein each $R^1$ may further be selected from =O and =NOR'; or (c) any pharmaceutical composition described herein.

In some embodiments, the condition requires modulation of sodium and/or calcium channel activity (e.g., $Na_v$ 1.7, $Na_v$ 1.8, and $Ca_v$ 3.2 channel activity, or any combination thereof of sodium and calcium channels).

In other embodiments, the condition is pain, epilepsy, migraine, Parkinson's disease, depression, schizophrenia, psychosis, or tinnitus.

In some embodiments, the pain is inflammatory pain or neuropathic pain.

In other embodiments, the pain is chronic pain. In further embodiments, the chronic pain is peripheral neuropathic pain (e.g., post-herpetic neuralgia, diabetic neuropathic pain, neuropathic cancer pain, failed back-surgery syndrome, trigeminal neuralgia, or phantom limb pain), central neuropathic pain (e.g., multiple sclerosis related pain, Parkinson disease related pain, post-stroke pain, post-traumatic spinal cord injury pain, or pain in dementia), musculoskeletal pain (e.g., osteoarthritic pain and fibromyalgia syndrome; inflammatory pain such as rheumatoid arthritis, or endometriosis), headache (e.g., migraine, cluster headache, tension headache syndrome, facial pain, or headache caused by other diseases), visceral pain (e.g., interstitial cystitis, irritable bowel syndrome, or chronic pelvic pain syndrome), or mixed pain (e.g., lower back pain, neck and shoulder pain, burning mouth syndrome, or complex regional pain syndrome).

In some embodiments, the pain is acute pain (e.g, nociceptive pain or post-operative pain).

Exemplary, non-limiting conditions modulated by sodium and/or calcium channel activity include pain, epilepsy, migraine, Parkinson's disease, depression, schizophrenia, psychosis, and tinnitus.

In another aspect, the invention relates to a method of modulating a voltage-gated sodium channel or a calcium channel, wherein said method comprises contacting a cell with (a) any of the compounds described herein (e.g. a compound according to Formula (I) or (II), or any of Compounds 1-3 and 5-13); or (b) a compound according to formula (III),

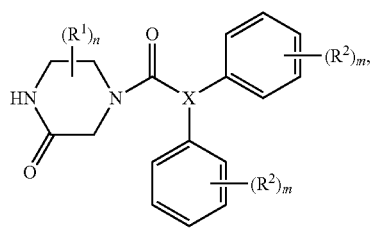

(III)

or a pharmaceutically acceptable salt, solvate, or prodrug thereof, or a stereoisomer thereof, or a conjugate thereof, where X is an optionally substituted alkylene (1-6C), alkenylene (2-6C), alkynylene (2-6C), heteroalkylene (2-6C), heteroalkenylene (2-6C), or heteroalkynylene (2-6C);

n is an integer between 0-6;

each m is, independently, an integer between 0-5;

each R' and $R^2$ is independently selected from halo, CN, $NO_2$, $CF_3$, $OCF_3$, COOR', $CONR'_2$, OR', SR', SOR', $SO_2R'$, $NR'_2$, NR'(CO)R', and $NR'SO_2R'$, wherein each R' is independently H or an optionally substituted group selected from alkyl (1-6C), alkenyl (2-6C), alkynyl (2-6C), heteroalkyl (2-6C) heteroalkenyl (2-6), and heteroalkynyl (2-6C); or the optional substituents may be one or more optionally substituted groups selected from alkyl (1-6C), alkenyl (2-6C), alkynyl (2-6C), heteroalkyl (2-6C), heteroalkenyl (2-6C), or heteroalkynyl (2-6C); and wherein each $R^1$ may further be selected from =O and =NOR'; or (c) any pharmaceutical composition described herein.

In some embodiments, the compound is

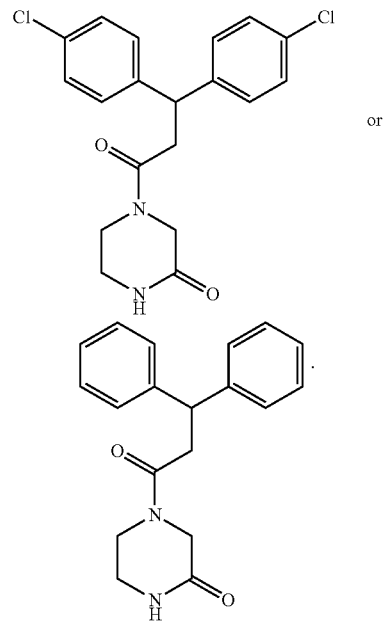

In some embodiments, two or more of the particularly described groups are combined into one compound.

In addition, the compounds of the invention may be coupled through conjugation to substances designed to alter the pharmacokinetics, for targeting, or for other reasons. Thus, the invention further includes conjugates of these compounds. For example, polyethylene glycol is often coupled to substances to enhance half-life; the compounds may be coupled to liposomes covalently or noncovalently or to other particulate carriers. They may also be coupled to targeting agents such as antibodies or peptidomimetics, often through linker moieties. Thus, the invention is also directed to the compounds of formula (1) when modified so as to be included in a conjugate of this type.

As used herein, the term "alkyl," "alkenyl" and "alkynyl" include straight-chain, branched-chain and cyclic monovalent substituents, as well as combinations of these, containing only C and H when unsubstituted. Examples include methyl, ethyl, isobutyl, cyclohexyl, cyclopentylethyl, 2-propenyl, 3-butynyl, and the like. Typically, the alkyl, alkenyl and alkynyl groups contain 1-8C (alkyl) or 2-8C (alkenyl or alkynyl). In some embodiments, they contain 1-6C, 1-4C, 1-3C or 1-2C (alkyl); or 2-6C, 2-4C or 2-3C (alkenyl or alkynyl). Further, any hydrogen atom on one of these groups can be replaced with a halogen atom, and in particular a fluoro or chloro, and still be within the scope of the definition of alkyl, alkenyl and alkynyl. For example, $CF_3$ is a 1C alkyl. These groups may be also be substituted by other substituents.

Heteroalkyl, heteroalkenyl and heteroalkynyl are similarly defined and contain at least one carbon atom but also contain one or more O, S or N heteroatoms or combinations thereof within the backbone residue whereby each heteroatom in the heteroalkyl, heteroalkenyl or heteroalkynyl group replaces one carbon atom of the alkyl, alkenyl or alkynyl group to which the heteroform corresponds. In preferred embodiments, the heteroalkyl, heteroalkenyl and heteroalkynyl groups have C at each terminus to which the group is attached to other groups, and the heteroatom(s) present are not located at a terminal position. As is understood in the art, these heteroforms do not contain more than three contiguous heteroatoms. In preferred embodiments, the heteroatom is O and/or N.

For greater certainty, to the extent that alkyl is defined as 1-6C, then the corresponding heteroalkyl contains for example, 1-5C, and at least one N, O, or S atom such that the heteroalkyl contains at least one C atom and at least one heteroatom. Similarly, when alkyl is defined as 1-6C or 1-4C, the heteroform would be 1-5C or 1-3C respectively, wherein at least one C is replaced by O, N or S. Accordingly, when alkenyl or alkynyl is defined as 2-6C (or 2-4C), then the corresponding heteroform would also contain 2-6C, N, O, or S atoms (or 2-4) since the heteroalkenyl or heteroalkynyl contains at least one carbon atom and at least one heteroatom. Further, heteroalkyl, heteroalkenyl or heteroalkynyl substituents may also contain one or more carbonyl groups. Examples of heteroalkyl, heteroalkenyl and heteroalkynyl groups include $CH_2OCH_3$, $CH_2N(CH_3)_2$, $CH_2OH$, $(CH_2)_nNR_2$, OR, COOR, $CONR_2$, $(CH_2)_nOR$, $(CH_2)_nCOR$, $(CH_2)_nCOOR$, $(CH_2)_nSR$, $(CH_2)_nSOR$, $(CH_2)_nSO_2R$, $(CH_2)_nCONR_2$, NRCOR, NRCOOR, $OCONR_2$, OCOR and the like wherein R is H or alkyl wherein the group contains at least one C and the size of the substituent is consistent with the definition of alkyl, alkenyl and alkynyl.

As used herein, the terms "alkylene," "alkenylene" and "alkynylene" refers to divalent or trivalent groups having a specified size, typically 1-2C, 1-3C, 1-4C, 1-6C or 1-8C for the saturated groups and 2-3C, 2-4C, 2-6C or 2-8C for the unsaturated groups. They include straight-chain, branched-chain and cyclic forms as well as combinations of these, containing only C and H when unsubstituted. Because these are at least divalent, they can link together two parts of a molecule, as exemplified by X in formula (1), which is trivalent, linking the carbonyl in formula (1) to two phenyl rings. Examples include methylene, ethylene, propylene, cyclopropan-1,1-diyl, ethylidene, 2-butene-1,4-diyl, and the like. These groups can be substituted by the groups typically suitable as substituents for alkyl, alkenyl and alkynyl groups as set forth herein. Thus C=O is a C1 alkylene that is substituted by =O, for example.

Heteroalkylene, heteroalkenylene and heteroalkynylene are similarly defined as divalent groups having a specified size, typically 1-3C, 1-4C, 1-6C or 1-8C for the saturated groups and 2-3C, 2-4C, 2-6C or 2-8C for the unsaturated groups. They include straight chain, branched chain and cyclic groups as well as combinations of these, and they further contain at least one carbon atom but also contain one or more O, S or N heteroatoms or combinations thereof within the backbone residue, whereby each heteroatom in the heteroalkylene, heteroalkenylene or heteroalkynylene group replaces one carbon atom of the alkylene, alkenylene or alkynylene group to which the heteroform corresponds. As is understood in the art, these heteroforms do not contain more than three contiguous heteroatoms.

"Aromatic" moiety or "aryl" moiety refers to any monocyclic or fused ring bicyclic system which has the characteristics of aromaticity in terms of electron distribution throughout the ring system and includes a monocyclic or fused bicyclic moiety such as phenyl or naphthyl; "heteroaromatic" or "heteroaryl" also refers to such monocyclic or fused bicyclic ring systems containing one or more heteroatoms selected from O, S and N. The inclusion of a heteroatom permits inclusion of 5-membered rings to be considered aromatic as well as 6-membered rings. Thus, typical aromatic/heteroaromatic systems include pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Because tautomers are theoretically possible, phthalimido is also considered aromatic. Typically, the ring systems contain 5-12 ring member atoms or 6-10 ring member atoms. In some embodiments, the aromatic or heteroaromatic moiety is a 6-membered aromatic rings system optionally containing 1-2 nitrogen atoms. More particularly, the moiety is an optionally substituted phenyl, 2-, 3- or 4-pyridyl, indolyl, 2- or 4-pyrimidyl, pyridazinyl, benzothiazolyl or benzimidazolyl. Even more particularly, such moiety is phenyl, pyridyl, or pyrimidyl and even more particularly, it is phenyl.

Halo may be any halogen atom, especially F, Cl, Br, or I, and more particularly it is fluoro or chloro.

In general, any alkyl, alkenyl, alkynyl, or aryl (including all heteroforms defined above) group contained in a substituent may itself optionally be substituted by additional substituents. The nature of these substituents is similar to those recited with regard to the substituents on the basic structures above. Thus, where an embodiment of a substituent is alkyl, this alkyl may optionally be substituted by the remaining substituents listed as substituents where this makes chemical sense, and where this does not undermine the size limit of alkyl per se; e.g., alkyl substituted by alkyl or by alkenyl would simply extend the upper limit of carbon atoms for these embodiments, and is not included. However, alkyl substituted by aryl, amino, halo and the like would be included. For example, where a group is substituted, the group may be substituted with 1, 2, 3, 4, 5, or 6 substituents. Optional substituents include, but are not limited to: 1C-6C alkyl or heteroaryl, 2C-6C alkenyl or heteroalkenyl, 2C-6C alkynyl or heteroalkynyl, halogen; aryl, heteroaryl, azido (—$N_3$), nitro (—$NO_2$), cyano (—CN), acyloxy(—OC(=O)R'), acyl (—C(=O)R'), alkoxy (—OR'), amido (—NR'C(=O)R" or —C(=O)NRR'), amino (—NRR'), carboxylic acid (—$CO_2H$), carboxylic ester (—$CO_2R'$), carbamoyl (—OC(=O)NR'R" or —NRC(=O)OR'), hydroxy (—OH), isocyano (—NC), sulfonate (—S(=O)$_2$OR), sulfonamide (—S(=O)$_2$NRR' or —NRS(=O)$_2$R'), or sulfonyl (—S(=O)$_2$R), where each R or R' is selected, independently, from H, 1C-6C alkyl or heteroaryl, 2C-6C alkenyl or heteroalkenyl, 2C-6C alkynyl or heteroalkynyl, aryl, or heteroaryl. A substituted group may have, for example, 1, 2, 3, 4, 5, 6, 7, 8, or 9 substituents.

The term an "effective amount" of an agent (e.g., a compound according to any of Formulas (I)-(III) or any of compounds 1-15), as used herein, is that amount sufficient to effect beneficial or desired results, such as clinical results, and, as such, an "effective amount" depends upon the context in which it is being applied. For example, in the context of administering an agent that is a modulator of sodium or calcium channels, an effective amount of an agent is, for example, an amount sufficient to achieve a change in sodium or calcium channel activity as compared to the response obtained without administration of the agent.

The term "pharmaceutical composition," as used herein, represents a composition containing a compound described herein (e.g., a compound according to any of Formulas (I)-(III) or any of compounds 1-15), formulated with a pharmaceutically acceptable excipient. In some embodiments, the pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

A "pharmaceutically acceptable excipient," as used herein, refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable prodrugs" as used herein, represents those prodrugs of the compounds of the present invention (e.g., a compound according to any of Formulas (I)-(III) or any of compounds 1-15) which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting the free base group with a suitable organic acid. Because some of the compounds described herein (e.g., a compound according to any of Formulas (I)-(III) or any of compounds 1-15) readily form acid addition salts and such salts may be advantageous for handling or stability, in some embodiments the compound is preferably in the form of a pharmaceutically acceptable salt.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable solvate" as used herein means a compound as described herein (e.g., a compound according to any of Formulas (I)-(III) or any of compounds 1-15) where molecules of a suitable solvent are incorporated in the crystal lattice. A suitable solvent is physiologically tolerable at the dosage administered. For example, solvates may be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the molecule is referred to as a "hydrate."

The term "prevent," as used herein, refers to prophylactic treatment or treatment that prevents one or more symptoms or conditions of a disease, disorder, or conditions described herein (for example, pain (e.g., chronic and acute pain), epilepsy, Alzheimer's disease, Parkinson's disease, cardiovascular disease, diabetes, cancer, sleep disorders, obesity, psychosis such as schizophrenia, overactive bladder, renal disease, neuroprotection, addiction, and male birth control).

Preventative treatment can be initiated, for example, prior to ("pre-exposure prophylaxis") or following ("post-exposure prophylaxis") an event that precedes the onset of the disease, disorder, or conditions. Preventive treatment that includes administration of a compound described herein (e.g., a compound according to any of Formulas (I)-(III) or any of compounds 1-15), or a pharmaceutically acceptable salt, solvate, or prodrug thereof, or a pharmaceutical composition thereof, can be acute, short-term, or chronic. The doses administered may be varied during the course of preventative treatment.

The term "prodrug," as used herein, represents compounds that are rapidly transformed in vivo to the parent compound of the above formula, for example, by hydrolysis in blood. Prodrugs of the compounds described herein may be conventional esters. Some common esters that have been utilized as prodrugs are phenyl esters, aliphatic (C1-C8 or C8-C24) esters, cholesterol esters, acyloxymethyl esters, carbamates, and amino acid esters. For example, a compound that contains an OH group may be acylated at this position in its prodrug form. A thorough discussion is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference. Preferably, prodrugs of the compounds of the present invention are suitable for use in contact with the tissues of humans and animals with undue toxicity, irritation, allergic response, and the like, commensurate with a reasonable benefit/risk ratio, and effective for their intended use.

As used herein, and as well understood in the art, "to treat" a condition or "treatment" of the condition (e.g., the conditions described herein such as chronic and acute pain, epilepsy, Alzheimer's disease, Parkinson's disease, cardiovascular disease, diabetes, cancer, sleep disorders, obesity, psychosis such as schizophrenia, overactive bladder, renal disease, neuroprotection, addiction, and male birth control) is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e., not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

The term "unit dosage form" refers to a physically discrete unit suitable as a unitary dosage for human subjects and other mammals, each unit containing a predetermined quantity of active material calculated to produce the desired therapeutic effect, in association with any suitable pharmaceutical excipient or excipients. Exemplary, non-limiting unit dosage forms include a tablet (e.g., a chewable tablet), caplet, capsule (e.g., a hard capsule or a soft capsule), lozenge, film, strip, gelcap, or syrup.

In some cases, the compounds of the invention contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed.

BRIEF DESCRIPTION OF THE DRAWING

FIG. 1 is a plot of the antiallodynic effects of compound 4 (i.p.) tested in SNL L5/L6 rats using the von Frey method at three different doses compared to vehicle alone.

DETAILED DESCRIPTION OF THE INVENTION

Compounds

One aspect of the invention is a method to use a compound of Formula (1) to treat a condition described herein that is associated with sodium and/or calcium channel function. These compounds include compounds of Formula (I):

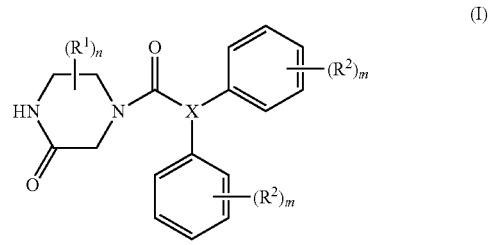

or a pharmaceutically acceptable salt, solvate, or prodrug thereof, or a stereoisomer thereof, or a conjugate thereof, where X is an optionally substituted alkylene (1-6C), alkenylene (2-6C), alkynylene (2-6C), heteroalkylene (2-6C), heteroalkenylene (2-6C), or heteroalkynylene (2-6C);

n is an integer between 0-6;

each m is, independently, an integer between 0-5;

wherein when n is 0 and X is $CH_2CH_2$, at least one m is not 0;

wherein when n is 1, each m is 0, and X is $CH_2$, $R^1$ is not $(CH_2)C_6H_5$, $(CH_2)_2C_6H_5$, or CONHR', where R' is optionally substituted alkyl (1-6C) or optionally substituted aryl;

each $R^1$ is, independently, selected from halo, CN, $NO_2$, $CF_3$, $OCF_3$, COOR', $CONR'_2$, OR', SR', SOR', $SO_2R'$, $NR'_2$, NR'(CO)R', and $NR'SO_2R'$, wherein each R' is independently H or an optionally substituted group selected from alkyl, alkenyl (2-6C), alkynyl (2-6C), heteroalkyl (2-6C) heteroalkenyl (2-6), and heteroalkynyl (2-6C); or each $R^1$ is selected from optionally substituted alkyl (1-6C), optionally substituted alkenyl (2-6C), optionally substituted alkynyl (2-6C), heteroalkyl (2-6C), optionally substituted heteroalkenyl (2-6C), optionally substituted heteroalkynyl (2-6C), =O, or =NOR'; and each $R^2$ is, independently, selected from halo, CN, $NO_2$, $CF_3$, $OCF_3$, COOR', $CONR'_2$, OR', SR', SOR', $SO_2R'$, $NR'_2$, NR'(CO)R', and $NR'SO_2R'$, wherein each R' is independently H or an optionally substituted group selected from alkyl (1-6C), alkenyl (2-6C), alkynyl (2-6C), heteroalkyl (2-6C) heteroalkenyl (2-6), and heteroalkynyl (2-6C); or each $R^2$ is an optionally substituted group selected from alkyl (1-6C), alkenyl (2-6C), alkynyl (2-6C), heteroalkyl (2-6C), heteroalkenyl (2-6C), or heteroalkynyl (2-6C).

Certain compounds of Formula (I) are described by Formula (II),

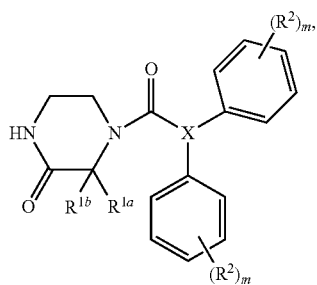

(II)

where each $R^{1a}$ and $R^{1b}$ is selected, independently, from H or unsubstituted 1C-6C alkyl; X is CH, CH$_2$CH, (CH$_2$)$_{2-4}$CH?, CH=C, NHCH, or CH$_2$S(=O)CH; each m is, independently, 0, 1, or 2; and each $R^2$ is, independently, optionally substituted 1C-6C alkyl or halogen.

Compounds according to Formula (III) are also described:

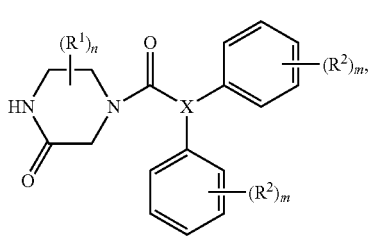

(III)

or a pharmaceutically acceptable salt, solvate, or prodrug thereof, or a stereoisomer thereof, or a conjugate thereof, where X is an optionally substituted alkylene (1-6C), alkenylene (2-6C), alkynylene (2-6C), heteroalkylene (2-6C), heteroalkenylene (2-6C), or heteroalkynylene (2-6C);

n is an integer between 0-6;

each m is, independently, an integer between 0-5;

each $R^1$ and $R^2$ is independently selected from halo, CN, NO$_2$, CF$_3$, OCF$_3$, COOR', CONR'$_2$, OR', SR', SOR', SO$_2$R', NR'$_2$, NR'(CO)R', and NR'SO$_2$R', wherein each R' is independently H or an optionally substituted group selected from alkyl (1-6C), alkenyl (2-6C), alkynyl (2-6C), heteroalkyl (2-6C) heteroalkenyl (2-6), and heteroalkynyl (2-6C); or the optional substituents may be one or more optionally substituted groups selected from alkyl (1-6C), alkenyl (2-6C), alkynyl (2-6C), heteroalkyl (2-6C), heteroalkenyl (2-6C), or heteroalkynyl (2-6C); and wherein each $R^1$ may further be selected from =O and =NOR'.

Exemplary compounds and methods of preparation of these compounds are described herein.

Modulation of Sodium Channels

The nine Na$_v$1 α-subunit isoforms Na$_v$1.7 and Na$_v$1.8 channel subtypes act as major contributors to both inflammatory and neuropathic pain (vide infra). Recently, mutations have been identified in the Na$_v$1.7 channel that lead either to a gain of channel function (Dib-Hajj et al., Brain 128:1847-1854, 2005) or more commonly to a loss of channel function (Chatelier et al., J. Neurophisiol. 99:2241-50, 2008). These mutations underlie human heritable disorders such as erythermalgia (Yang et al., J Med Genet. 41(3) 171-4, 2004), paroxysmal extreme pain disorder (Fertleman et al., Neuron. 52(5) 767-74, 2006), and congenital indifference to pain (Cox et al., Nature 444(7121):894-8, 2006). Behavioral studies have shown in mice that inflammatory and acute mechanosensory pain is reduced when Na$_v$1.7 is knocked out in Na$_v$1.8-positive neurons (Nassar et al., Proc Natl Acad Sci USA. 101(34): 12706-11, 2004). In addition, siRNA of Na$_v$1.7 attenuates inflammatory hyperalgesia (Yeomans et al., Hum Gene Ther. 16(2) 271-7, 2005). The role of Na$_v$1.8 in inflammatory (Khasar et al. Neurosci Lett. 256(1):17-20, 1998), neuropathic and mechanical hyperalgesia (Joshi et al., Pain 123(1-2):75-82, 2006) has also emerged using molecular techniques to knockdown Na$_v$ 1.8, which has been shown to reduce the maintenance of these different pain states.

Lacosamide is a functionalized amino acid that has shown effectiveness as an analgesic in several animal models of neuropathic pain and is currently in late stages of clinical development for epilepsy and diabetic neuropathic pain. One mode of action that has been validated for lacosamide is inhibition of voltage-gated sodium channel activity by selective inhibition with the slow-inactivated conformation of the channel (Sheets et al., Journal of Pharmacology and Experimental Therapeutics, 326(1) 89-99 (2008)). Modulators of sodium channels, including clinically relevant compounds, can exhibit a pronounced state-dependent binding, where sodium channels that are rapidly and repeatedly activated and inactivated are more readily blocked. In a simplified scheme, voltage-gated sodium channels have four distinct states: open, closed, fast-inactivated and slow-inactivated. Classic sodium channel modulators, such as lidocaine, are believed to exhibit the highest affinity for the fast-inactivated state. However, alteration of the slow inactivated state is also clinically relevant.

Modulation of Calcium Channels

The entry of calcium into cells through voltage-gated calcium channels mediates a wide variety of cellular and physiological responses, including excitation-contraction coupling, hormone secretion and gene expression (e.g., Miller et al., Science 235:46-52 (1987); Augustine et al., Annu Rev Neurosci 10: 633-693 (1987)). In neurons, calcium channels directly affect membrane potential and contribute to electrical properties such as excitability, repetitive firing patterns and pacemaker activity. Calcium entry further affects neuronal functions by directly regulating calcium-dependent ion channels and modulating the activity of calcium-dependent enzymes such as protein kinase C and calmodulin-dependent protein kinase II. An increase in calcium concentration at the presynaptic nerve terminal triggers the release of neurotransmitter, which also affects neurite outgrowth and growth cone migration in developing neurons.

Calcium channels mediate a variety of normal physiological functions, and are also implicated in a number of human disorders as described herein. For example, calcium channels also have been shown to mediate the development and maintenance of the neuronal sensitization and hyperexcitability processes associated with neuropathic pain, and provide attractive targets for the development of analgesic drugs (reviewed in Vanegas et al., Pain 85: 9-18 (2000)). Native calcium channels have been classified by their electrophysiological and pharmacological properties into T-, L-, N-, P/Q- and R-types (reviewed in Catterall, Annu Rev Cell Dev Biol 16: 521-555, 2000; Huguenard, Annu Rev Physiol 58: 329-348, 1996). The L-, N- and P/Q-type channels activate at more positive potentials (high voltage-activated) and display diverse kinetics and voltage-dependent properties (Id.). T-type channels can be distinguished by having a more negative range of activation and inactivation, rapid inactivation, slow deactivation, and smaller single-channel conductances. There are three subtypes of T-type calcium channels that have been molecularly, pharmacologically, and elecrophysiologically identified: these subtypes have been termed $\alpha_{1G}$, $\alpha_{1H}$, and $\alpha_{1I}$ (alternately called Cav 3.1, Cav 3.2 and Cav 3.3 respectively).

T-type calcium channels are involved in various medical conditions. In mice lacking the gene expressing the 3.1 subunit, resistance to absence seizures was observed (Kim et al., *Mol. Cell Neurosci.* 18(2): 235-245 (2001)). Other studies have also implicated the 3.2 subunit in the development of epilepsy (Su et al., *J. Neurosci.* 22: 3645-3655 (2002)). There is also evidence that some existing anticonvulsant drugs, such as ethosuximide, function through the blockade of T-type channels (Gomora et al., *Mol. Pharmacol.* 60: 1121-1132 (2001)).

Low voltage-activated calcium channels are highly expressed in tissues of the cardiovascular system. There is also a growing body of evidence that suggests that T-type calcium channels are abnormally expressed in cancerous cells and that blockade of these channels may reduce cell proliferation in addition to inducing apoptosis. Recent studies also show that the expression of T-type calcium channels in breast cancer cells is proliferation state dependent, i.e. the channels are expressed at higher levels during the fast-replication period, and once the cells are in a non-proliferation state, expression of this channel is minimal. Therefore, selectively blocking calcium channel entry into cancerous cells may be a valuable approach for preventing tumor growth (e.g., PCT Patent Application Nos. WO 05/086971 and WO 05/77082; Taylor et al., *World J. Gastroenterol.* 14(32): 4984-4991 (2008); Heo et al., *Biorganic & Medicinal Chemistry Letters* 18:3899-3901 (2008)).

T-type calcium channels may also be involved in still other conditions. A recent study also has shown that T-type calcium channel antagonists inhibit high-fat diet-induced weight gain in mice. In addition, administration of a selective T-type channel antagonist reduced body weight and fat mass while concurrently increasing lean muscle mass (e.g., Uebele et al., *The Journal of Clinical Investigation*, 119(6):1659-1667 (2009)). T-type calcium channels may also be involved in pain (see for example: US Patent Publication No. 2003/0086980; PCT Publication Nos. WO 03/007953 and WO 04/000311). In addition to cardiovascular disease, epilepsy (see also US Patent Application No. 2006/0025397), cancer, and chronic or acute pain, T-type calcium channels have been implicated in diabetes (US Patent Publication No. 2003/0125269), sleep disorders (US Patent Publication No. 2006/0003985), Parkinson's disease and psychosis such as schizophrenia (US Patent Publication No. 2003/0087799); overactive bladder (Sui et al., *British Journal of Urology International* 99(2): 436-441 (2007); US Patent Publication No. 2004/0197825), renal disease (Hayashi et al., *Journal of Pharmacological Sciences* 99: 221-227 (2005)), anxiety and alcoholism (US Patent Publication No. 2009/0126031), neuroprotection, and male birth control.

The modulation of ion channels by the compounds described herein (e.g., a compound according to any of Formulas (I)-(XI) or any of Compounds 1-23) can be measured according to methods known in the art (e.g., in the references provided herein). Modulators of ion channels, e.g., voltage gated sodium and calcium ion channels, and the medicinal chemistry or methods by which such compounds can be identified, are also described in, for example: Birch et al., *Drug Discovery Today*, 9(9):410-418 (2004); Audesirk, "Chapter 6—Electrophysiological Analysis of Ion Channel Function," *Neurotoxicology: Approaches and Methods*, 137-156 (1995); Camerino et al., "Chapter 4: Therapeutic Approaches to Ion Channel Diseases," *Advances in Genetics*, 64:81-145 (2008); Petkov, "Chapter 16—Ion Channels," *Pharmacology: Principles and Practice*, 387-427 (2009); Standen et al., "Chapter 15—Patch Clamping Methods and Analysis of Ion Channels," *Principles of Medical Biology*, Vol. 7, Part 2, 355-375 (1997); Xu et al., *Drug Discovery Today*, 6(24):1278-1287 (2001); and Sullivan et al., *Methods Mol. Biol.* 114:125-133 (1999). Exemplary experimental methods are also provided in the Examples.

Diseases and Conditions

Exemplary conditions that can be treated using the compounds described herein include pain (e.g., chronic or acute pain), epilepsy, Alzheimer's disease, Parkinson's disease, diabetes; cancer; sleep disorders; obesity; psychosis such as schizophrenia; overactive bladder; renal disease, neuroprotection, and addiction. For example, the conidition can be pain (e.g., neuropathic pain or post-surgery pain), epilepsy, migraine, Parkinson's disease, depression, schizophrenia, psychosis, or tinnitus.

Epilepsy as used herein includes but is not limited to partial seizures such as temporal lobe epilepsy, absence seizures, generalized seizures, and tonic/clonic seizures.

Cancer as used herein includes but is not limited to breast carcinoma, neuroblastoma, retinoblastoma, glioma, prostate carcinoma, esophageal carcinoma, fibrosarcoma, colorectal carcinoma, pheochromocytoma, adrenocarcinoma, insulinoma, lung carcinoma, melanoma, and ovarian cancer.

Acute pain as used herein includes but is not limited to nociceptive pain and post-operative pain. Chronic pain includes but is not limited by: peripheral neuropathic pain such as post-herpetic neuralgia, diabetic neuropathic pain, neuropathic cancer pain, failed back-surgery syndrome, trigeminal neuralgia, and phantom limb pain; central neuropathic pain such as multiple sclerosis related pain, Parkinson disease related pain, post-stroke pain, post-traumatic spinal cord injury pain, and pain in dementia; musculoskeletal pain such as osteoarthritic pain and fibromyalgia syndrome; inflammatory pain such as rheumatoid arthritis and endometriosis; headache such as migraine, cluster headache, tension headache syndrome, facial pain, headache caused by other diseases; visceral pain such as interstitial cystitis, irritable bowel syndrome and chronic pelvic pain syndrome; and mixed pain such as lower back pain, neck and shoulder pain, burning mouth syndrome and complex regional pain syndrome.

In treating osteoarthritic pain, joint mobility can also improve as the underlying chronic pain is reduced. Thus, use of compounds of the present invention to treat osteoarthritic pain inherently includes use of such compounds to improve joint mobility in patients suffering from osteoarthritis.

The compounds described herein can be tested for efficacy in any standard animal model of pain. Various models test the sensitivity of normal animals to intense or noxious stimuli (physiological or nociceptive pain). These tests include responses to thermal, mechanical, or chemical stimuli. Thermal stimuli usually involve the application of hot stimuli (typically varying between 42-55° C.) including, for example: radiant heat to the tail (the tail flick test), radiant heat to the plantar surface of the hindpaw (the Hargreaves test), the hotplate test, and immersion of the hindpaw or tail into hot water Immersion in cold water, acetone evaporation, or cold plate tests may also be used to test cold pain responsiveness. Tests involving mechanical stimuli typically measure the threshold for eliciting a withdrawal reflex of the hindpaw to graded strength monofilament von Frey hairs or to a sustained pressure stimulus to a paw (e.g., the Ugo Basile analgesiometer). The duration of a response to a standard pinprick may also be measured. When using a chemical stimulus, the response to the application or injection of a chemical irritant (e.g., capsaicin, mustard oil, bradykinin, ATP, formalin, acetic acid) to the skin, muscle joints or internal organs (e.g., bladder or peritoneum) is measured.

In addition, various tests assess pain sensitization by measuring changes in the excitability of the peripheral or central components of the pain neural pathway. In this regard, peripheral sensitization (i.e., changes in the threshold and responsiveness of high threshold nociceptors) can be induced by repeated heat stimuli as well as the application or injection of sensitizing chemicals (e.g., prostaglandins, bradykinin, histamine, serotonin, capsaicin, or mustard oil). Central sensitization (i.e., changes in the excitability of neurons in the central nervous system induced by activity in peripheral pain fibers) can be induced by noxious stimuli (e.g., heat), chemical stimuli (e.g., injection or application of chemical irritants), or electrical activation of sensory fibers.

Various pain tests developed to measure the effect of peripheral inflammation on pain sensitivity can also be used to study the efficacy of the compounds (Stein et al., *Pharmacol. Biochem. Behav.* (1988) 31: 445-451; Woolf et al., *Neurosci.* (1994) 62: 327-331). Additionally, various tests assess peripheral neuropathic pain using lesions of the peripheral nervous system. One such example is the "axotomy pain model" (Watson, *J. Physiol.* (1973) 231:41). Other similar tests include the SNL test which involves the ligation of a spinal segmental nerve (Kim and Chung *Pain* (1992) 50: 355), the Seltzer model involving partial nerve injury (Seltzer, *Pain* (1990) 43: 205-18), the spared nerve injury (SNI) model (Decosterd and Woolf, *Pain* (2000) 87:149), chronic constriction injury (CCI) model (Bennett (1993) *Muscle Nerve* 16: 1040), tests involving toxic neuropathies such as diabetes (streptozocin model), pyridoxine neuropathy, taxol, vincristine, and other antineoplastic agent-induced neuropathies, tests involving ischaemia to a nerve, peripheral neuritis models (e.g., CFA applied peri-neurally), models of post-herpetic neuralgia using HSV infection, and compression models.

In all of the above tests, outcome measures may be assessed, for example, according to behavior, electrophysiology, neurochemistry, or imaging techniques to detect changes in neural activity.

Exemplary models of pain are also described in the Examples provided herein.

In addition to being able to modulate a particular sodium or calcium channel, it may be desirable that the compound has very low activity with respect to the hERG $K^+$ channel, which is expressed in the heart: compounds that block this channel with high potency may cause reactions which are fatal. See, e.g., Bowlby et al., "hERG (KCNH2 or $K_v11.1$ $K^+$ Channels: Screening for Cardiac Arrhythmia Risk," *Curr. Drug Metab.* 9(9):965-70 (2008)). Thus, for a compound that modulates the sodium or calcium channel, it may also be shown that the hERG $K^+$ channel is not inhibited or only minimally inhibited as compared to the inhibition of the primary channel targeted. Similarly, it may be desirable that the compound does not inhibit cytochrome p450, an enzyme that is required for drug detoxification. Such compounds may be particularly useful in the methods described herein. Exemplary compounds have been Pharmaceutical Compositions For use as treatment of human and animal subjects, the compounds of the invention can be formulated as pharmaceutical or veterinary compositions. Depending on the subject to be treated, the mode of administration, and the type of treatment desired—e.g., prevention, prophylaxis, or therapy—the compounds are formulated in ways consonant with these parameters. A summary of such techniques is found in *Remington: The Science and Practice of Pharmacy*, 21$^{st}$ Edition, Lippincott Williams & Wilkins, (2005); and *Encyclopedia of Pharmaceutical Technology*, eds. J. Swarbrick and J. C. Boylan, 1988-1999, Marcel Dekker, New York, each of which is incorporated herein by reference.

The compounds described herein (e.g., a compound according to any of Formulas (I)-(III) or any of compounds 1-15) may be present in amounts totaling 1-95% by weight of the total weight of the composition. The composition may be provided in a dosage form that is suitable for intraarticular, oral, parenteral (e.g., intravenous, intramuscular), rectal, cutaneous, subcutaneous, topical, transdermal, sublingual, nasal, vaginal, intravesicular, intraurethral, intrathecal, epidural, aural, or ocular administration, or by injection, inhalation, or direct contact with the nasal, genitourinary, gastrointesitnal, reproductive or oral mucosa. Thus, the pharmaceutical composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, preparations suitable for iontophoretic delivery, or aerosols. The compositions may be formulated according to conventional pharmaceutical practice.

In general, for use in treatment, a compound described herein (e.g., a compound according to any of Formulas (I)-(III) or any of compounds 1-15) may be used alone, as mixtures of two or more compounds, or in combination with other pharmaceuticals. An example of other potential pharmaceuticals to combine with a compound described herein (e.g., a compound according to any of Formulas (I)-(III) or any of compounds 1-15) would include pharmaceuticals for the treatment of the same indication. For example, in the treatment of pain, a compound may be combined with another pain relief treatment such as an NSAID, or a compound which selectively inhibits COX-2, or an opioid, or an adjuvant analgesic such as an antidepressant. Another example of a potential pharmaceutical to combine with the compounds described herein (e.g., a compound according to any of Formulas (I)-(XI) or any of Compounds 1-23) would include pharmaceuticals for the treatment of different yet associated or related symptoms or indications. Depending on the mode of administration, the compounds will be formulated into suitable compositions to permit facile delivery. Each compound of a combination therapy may be formulated in a variety of ways that are known in the art. For example, the first and second agents of the combination therapy may be formulated together or separately. Desirably, the first and second agents are formulated together for the simultaneous or near simultaneous administration of the agents.

The compounds of the invention may be prepared and used as pharmaceutical compositions comprising an effective amount of a compound described herein (e.g., a compound according to any of Formulas (I)-(III) or any of compounds 1-15) and a pharmaceutically acceptable carrier or excipient, as is well known in the art. In some embodiments, the composition includes at least two different pharmaceutically acceptable excipients or carriers.

Formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised. See, for example, U.S. Pat. No. 5,624,677, which is herein incorporated by reference.

Systemic administration may also include relatively non-invasive methods such as the use of suppositories, transdermal patches, transmucosal delivery and intranasal administration. Oral administration is also suitable for compounds of the invention. Suitable forms include syrups, capsules, and tablets, as is understood in the art.

For administration to animal or human subjects, the dosage of the compounds of the invention may be, for example, 0.01-50 mg/kg (e.g., 0.01-15 mg/kg or 0.1-10 mg/kg). For example, the dosage can be 10-30 mg/kg.

Each compound of a combination therapy, as described herein, may be formulated in a variety of ways that are known in the art. For example, the first and second agents of the combination therapy may be formulated together or separately.

The individually or separately formulated agents can be packaged together as a kit. Non-limiting examples include, but are not limited to, kits that contain, e.g., two pills, a pill and a powder, a suppository and a liquid in a vial, two topical creams, etc. The kit can include optional components that aid in the administration of the unit dose to patients, such as vials for reconstituting powder forms, syringes for injection, customized IV delivery systems, inhalers, etc. Additionally, the unit dose kit can contain instructions for preparation and administration of the compositions. The kit may be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

Solid Dosage Forms for Oral Use

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Two or more compounds may be mixed together in a tablet, capsule, or other vehicle, or may be partitioned. In one example, the first compound is contained on the inside of the tablet, and the second compound is on the outside, such that a substantial portion of the second compound is released prior to the release of the first compound.

Formulations for oral use may also be provided as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Generally, when administered to a human, the oral dosage of any of the compounds of the combination of the invention will depend on the nature of the compound, and can readily be determined by one skilled in the art. Typically, such dosage is normally about 0.001 mg to 2000 mg per day, desirably about 1 mg to 1000 mg per day, and more desirably about 5 mg to 500 mg per day. Dosages up to 200 mg per day may be necessary.

Administration of each drug in a combination therapy, as described herein, can, independently, be one to four times daily for one day to one year, and may even be for the life of the patient. Chronic, long-term administration may be indicated.

Synthesis of the Invention Compounds

The reaction scheme and Examples are intended to illustrate the synthesis of a representative number of compounds. Accordingly, the Examples are intended to illustrate but not to limit the invention. Additional compounds not specifically exemplified may be synthesized using conventional methods in combination with the methods described herein.

The compounds described herein can be prepared using methods known in the art, e.g., according to Scheme 1.

Scheme 1

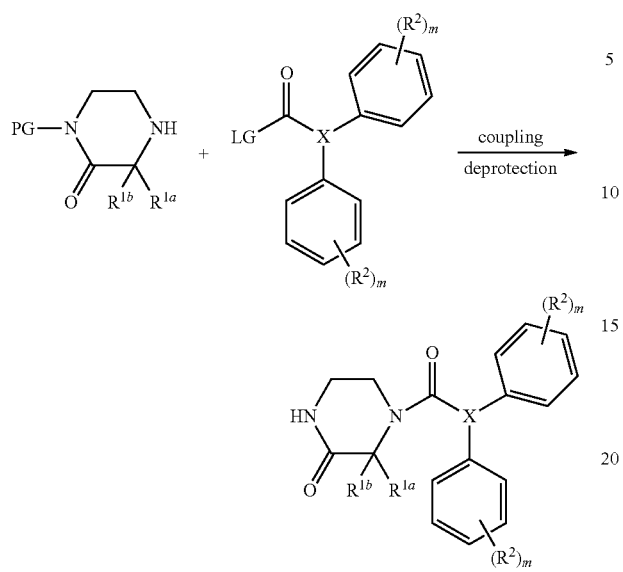

In Scheme 1, PG may be H or an N-protecting group. The term "N-protecting group," as used herein, represents those groups intended to protect an amino group against undesirable reactions during synthetic procedures. Commonly used N-protecting groups are disclosed in Greene, "Protective Groups In Organic Synthesis," $3^{rd}$ Edition (John Wiley & Sons, New York, 1999), which is incorporated herein by reference. N-protecting groups include acyl, aryloyl, or carbamyl groups; sulfonyl-containing groups; carbamate forming group; alkaryl groups such as benzyl; and silyl groups. Exemplary N-protecting groups include formyl, acetyl, benzoyl, pivaloyl, t-butylacetyl, alanyl, phenylsulfonyl, benzyl, t-butyloxycarbonyl (Boc), and benzyloxycarbonyl (Cbz).

EXAMPLES

Example 1

Synthesis of 4-(3,3-diphenylpropanoyl)piperazin-2-one (Compound 4)

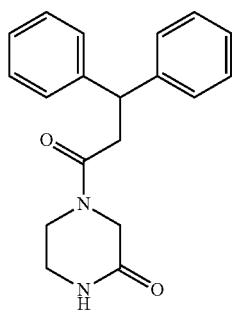 [SMILES: O=C1CN(C(=O)CC(c2ccccc2)c2ccccc2)CCN1]

To a solution of piperazin-2-one (100 m g, 1 mmol), 3,3-diphenylpropanoic acid (226 mg, 1 mmol) was added EDC (382 mg, 2 mmol) in dichloromethane (5 mL). The solution was stirred at room temperature overnight and concentrated in vacuo. The residue was diluted with EtOAc, and the mixture was washed consecutively with saturated aqueous $NaHCO_3$ and brine. The organic layer was dried ($Na_2SO_4$), filtered, and concentrated in vacuo. The crude material was purified by flash column chromatography (2:98 MeOH/DCM) to give the desired 4-(3,3-diphenylpropanoyl)piperazin-2-one product (compound 4) (246 mg, 80%) as a white powder.

Example 2

Synthesis of Acid Intermediates

Additional acid intermediates were also synthesized as follows:

A. Synthesis of 3,3-diphenylacrylic acid (Intermediate in Synthesis of Compound 8)

A(i) Synthesis of 3,3-diphenylacrylonitrile

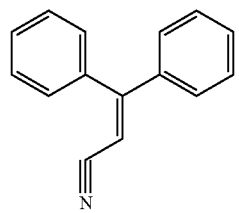 [SMILES: N#CC=C(c1ccccc1)c1ccccc1]

To a solution of benzophenone (9.1 g, 50 mmol) in acetonitrile (20 mL) was added potassium hydroxide (3.3 g, 50 mmol) in acetonitrile (25 mL). The solution was refluxed for 8 hours. The hot reaction mixture was poured into 100 g crushed ice and then extracted with dichloromethane. The organic extract was washed with water, dried over sodium sulfate, and concentrated in vacuo. The crude material was purified by flash column chromatography (diethyl ether/hexanes) to give 3,3-diphenylacrylonitrile (7.7 g, 73.3%) as an oil.

A(ii) Synthesis of 3,3-diphenylacrylic acid

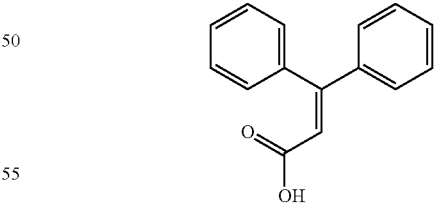

A mixture of 3,3-diphenylacrylonitrile (5.76 g, 28.1 mmol) and sodium hydroxide (11.2 g) in ethylene glycol (180 mL) and water (1 mL) were refluxed for 3 days. The reaction mixture was diluted with water (100 mL), acidified with 5N HCl to pH~1, and extracted with ethyl acetate. The organic extract was washed with water, dried over sodium sulfate, and concentrated in vacuo. The crude material was purified by flash column chromatography ethyl acetate/hexanes to give 3,3-diphenylacrylic acid (5.1 g, 81%) as a white powder.

B. Synthesis of 3,3-di-o-tolylpropanoic acid (Intermediate in Synthesis of Compound 5)

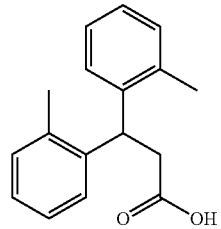 [SMILES: Cc1ccccc1C(CC(=O)O)c1ccccc1C]

O-Tolylaldehyde (10 g, 83.2 mmol), ethylcyanoacetate (9.4 g, 83.2 mmol), and piperidine (1.1 mL, 11 mmol) were heated in toluene at reflux for 1 hour. The reaction was washed with $H_2O$ and brine, dried over $MgSO_4$, and concentrated, with the resulting residue purified by chromatography (10-50% EtOAc, petroleum ether) to give ethyl 2-cyano-3-o-tolylacrylate (10.6 g, 59%).

This intermediate was stirred in toluene under $N_2$ and o-tolylmagnesium bromide (2.0 M solution in $Et_2O$, 27 mL, 54 mmol) was added. The reaction heated at reflux for 1 hour. After cooling, the reaction was quenched with 1 M HCl (40 mL). The organic layer was separated, washed with $H_2O$, dried over $MgSO_4$, and concentrated in-vacuo. Ethyl 2-cyano-3,3-di-tolylacrylate was precipitated from the residue with 10% EtOAc/PE, and the resulting solid was collected by filtration to give the next intermediate (13.7 g, 88%).

The intermediate was heated in $H_2O:H_2SO_4:AcOH$ (160 mL:80 mL:80 mL) at reflux for 16 hours. The reaction was tipped over ice/water (400 mL), and the resultant precipitate was collected by filtration. The solid was purified by column chromatography (5% MeOH/DCM) to give the required 3,3-di-o-tolylpropanoic acid (6.8 g, 62%).

C. Synthesis of 2-(benzhydrylsulfinyl)acetic acid

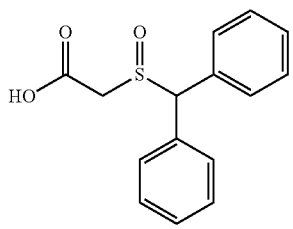 [SMILES: O=C(O)CS(=O)C(c1ccccc1)c1ccccc1]

10 g of thiourea was dissolved in 57 mL of 48% HBr and 10 ml of water. The reaction mixture was heated to 60° C., and 20.2 g of benzhydrol was added. The temperature was increased to 90° C., and the mixture was then cooled to room temperature. The crystals were filtered off and washed with water. To the above crystals were added 35 mL 30% sodium hydroxide. The mixture was heated to 70° C., and 11.44 g chloroacetic acid in 22 mL of water were added slowly. The mixture was refluxed for half an hour after the addition. 14.3 mL hydrogen peroxide (30%) was added to the above solution within 3 hours at room temperature. Water (22 ml) was added to the reaction mixture, which was then filtered. The filtrate was acidified with concentrated HCl (d=1.18). The resulting solid was filtered and dried to give 2-(benzhydrylsulfinyl)acetic acid (13 g, 43%) as the desired product.

Example 3

Synthesis of
N-benzhydryl-3-oxopiperazine-1-carboxamide
(Compound 1)

To a solution of piperazin-2-one (100 mg, 1 mmol) was added (isocyanatomethylene)dibenzene (209 mg, 1 mmol) in dichloromethane (5 mL). The solution was stirred for 2 hours at room temperature and concentrated in vacuo. The residue was diluted with EtOAc and then washed consecutively with saturated aqueous $NaHCO_3$ and brine. The organic layer was dried ($Na_2SO_4$), filtered, and concentrated in vacuo. The crude material was purified by flash column chromatography (2:98 MeOH/DCM) to give desired compound N-benzhydryl-3-oxopiperazine-1-carboxamide (Compound 1) (232 mg, 75%) as a white powder.

Example 4

Mass Spectrometric Analysis

Following the general procedures set forth in Examples 1-3, the following compounds listed in Table 2 below were prepared. Mass spectrometry was employed with the final compound and at various stages throughout the synthesis as a confirmation of the identity of the product obtained (M+1). For the mass spectrometric analysis, samples were prepared at an approximate concentration of 1 μg/mL in acetonitrile with 0.1% formic acid. Samples were then manually infused into an Applied Biosystems API3000 triple quadrupole mass spectrometer and scanned in Q1 in the range of 50 to 700 m/z.

TABLE 2

| Compound No. | Name | Structure | Mass Spec (m/z) |
|---|---|---|---|
| 1 | N-benzhydryl-3-oxopiperazine-1-carboxamide | 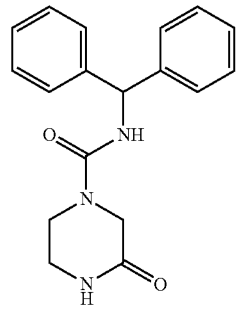 | 310.1 |
| 2 | 4-(2-(benzhydrylsulfinyl)acetyl)piperazin-2-one | 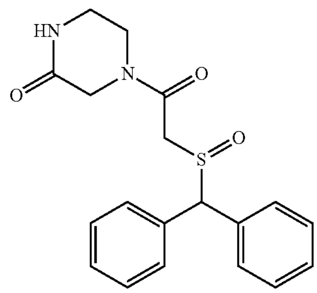 [SMILES: O=C1CN(C(=O)CS(=O)C(c2ccccc2)c2ccccc2)CCN1] | 357.1 |
| 3 | 4-(3,3-bis(4-chlorophenyl)propanoyl)piperazin-2-one | 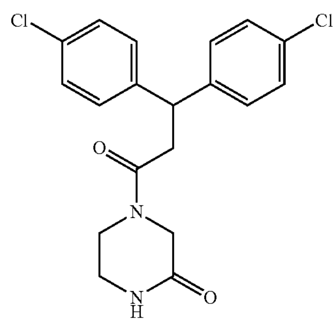 [SMILES: O=C1CN(C(=O)CC(c2ccc(Cl)cc2)c2ccc(Cl)cc2)CCN1] | 377.2 |
| 4 | 4-(3,3-diphenylpropanoyl)piperazin-2-one | 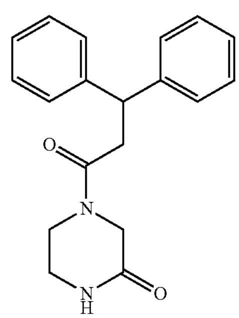 [SMILES: O=C1CN(C(=O)CC(c2ccccc2)c2ccccc2)CCN1] | 309.2 |
| 5 | 4-(3,3-di-tolylpropanoyl)piperazin-2-one | 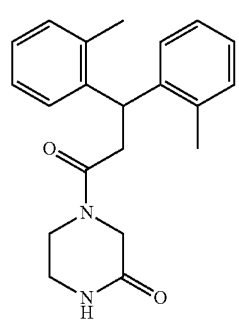 [SMILES: Cc1ccccc1C(CC(=O)N1CCNC(=O)C1)c1ccccc1C] | 337.2 |

TABLE 2-continued

| Compound No. | Name | Structure | Mass Spec (m/z) |
|---|---|---|---|
| 6 | 4-(6,6-diphenylhexanoyl)piperazin-2-one | 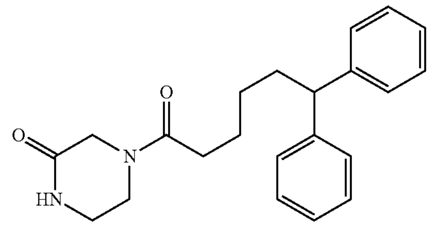 [SMILES: O=C1CN(C(=O)CCCCC(c2ccccc2)c2ccccc2)CCN1] | 351.2 |
| 7 | 4-(2,2-diphenylacetyl)piperazin-2-one | 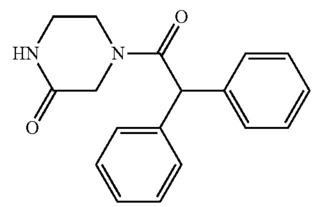 [SMILES: O=C1CN(C(=O)C(c2ccccc2)c2ccccc2)CCN1] | 295.1 |
| 8 | 4-(3,3-diphenylacryloyl)piperazin-2-one | 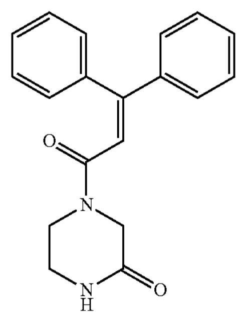 [SMILES: O=C1CN(C(=O)C=C(c2ccccc2)c2ccccc2)CCN1] | 307.1 |
| 9 | 4-(3,3-bis(4-fluorophenyl)propanoyl)piperazin-2-one | 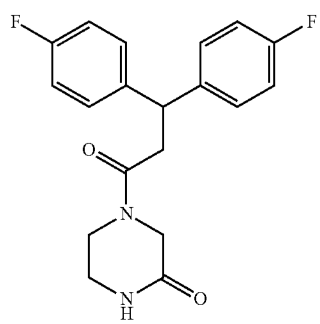 [SMILES: O=C1CN(C(=O)CC(c2ccc(F)cc2)c2ccc(F)cc2)CCN1] | 345.1 |
| 10 | 4-(3,3-diphenylpropanoyl)-3,3-dimethylpiperazin-2-one | 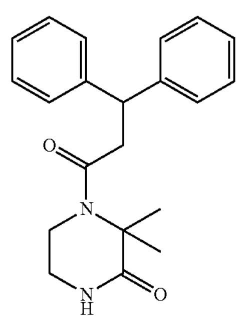 [SMILES: CC1(C)C(=O)NCCN1C(=O)CC(c1ccccc1)c1ccccc1] | 337.2 |

TABLE 2-continued

| Compound No. | Name | Structure | Mass Spec (m/z) |
|---|---|---|---|
| 11 | (R)-4-(3,3-diphenyl propanoyl)-3-methylpiperazin-2-one | 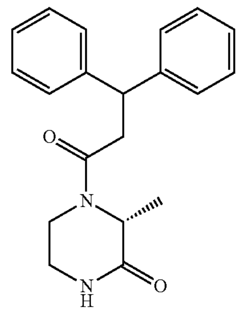 [SMILES: C[C@@H]1C(=O)NCCN1C(=O)CC(c1ccccc1)c1ccccc1] | 323.2 |
| 12 | (S)-4-(3,3-diphenyl propanoyl)-3-methylpiperazin-2-one | 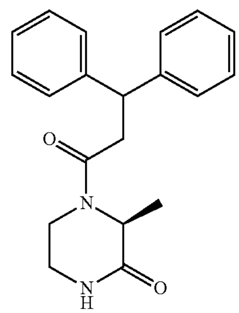 [SMILES: C[C@H]1C(=O)NCCN1C(=O)CC(c1ccccc1)c1ccccc1] | 323.2 |
| 13 | 4-(2,2-bis(4-chlorophenyl) acetyl)piperazin-2-one | 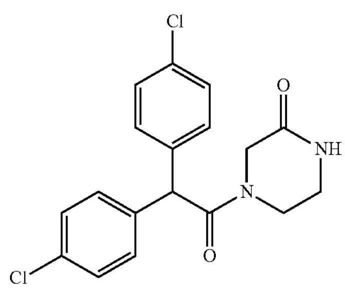 [SMILES: O=C1CN(C(=O)C(c2ccc(Cl)cc2)c2ccc(Cl)cc2)CCN1] | 363.24 |
| 14 | 4-(2-(diphenylamino) acetyl)piperazin-2-one | 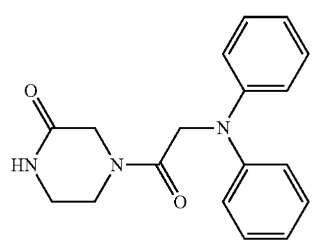 [SMILES: O=C1CN(C(=O)CN(c2ccccc2)c2ccccc2)CCN1] | 309.36 |
| 15 | 4-(3,3-bis(4-fluorophenyl) propanoyl)-3,3-dimethylpiperazin-2-one | 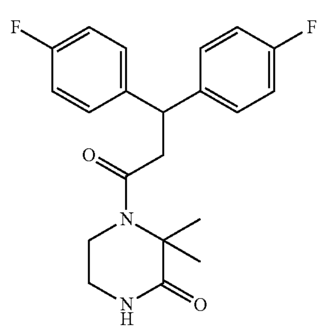 [SMILES: CC1(C)C(=O)NCCN1C(=O)CC(c1ccc(F)cc1)c1ccc(F)cc1] | 372.41 |

Example 5

$Ca_v3.2$ Voltage-Clamp Electrophysiological Assays

Prior to recording currents from $Ca_v3.2$ T-type $Ca^{2+}$ channels expressed in HEK cells, the culture media was replaced with extracellular solution (ECS) containing (in mM): 142 CsCl, 10 D-glucose, 2 $CaCl_2$, 1 $MgCl_2$, 10 HEPES, pH adjusted to 7.4 with CsOH. Borosilicate glass patch pipettes, pulled on a P-97 micropipette puller (Sutter Instruments, Novato, Calif.) with typical resistances of 2-4 MW, were backfilled with intracellular solution containing (in mM): 126.5 Cs-methanesulphonate, 2 $MgCl_2$, 10 HEPES, 11 EGTA, 2 Na-ATP, pH adjusted to 7.3 CsOH. Voltages were recorded in the whole-cell configuration at room temperature (~21° C.) using an Axopatch 200B (Molecular Devices, Sunnyvale, Calif.) patch-clamp amplifier. Recordings were low-pass filtered at 1 kHz (−3 dB 4-pole Bessel filter), digitized at 2 kHz with a Digidata 1322A interface (Molecular Devices), and acquired using pClamp 9.2 (Molecular Devices). No leak subtraction was used. Test compounds, prepared as 30 mM stock solutions in DMSO and diluted in extracellular buffer, were applied through a gravity driven multi-barrelled array of capillaries (24 gauge) connected to reservoirs controlled by solenoid valves. The effects of compounds on $Ca_v3.2$ slow and fast inactivation were evaluated using four different voltage protocols. The voltage dependence of fast and slow channel inactivation was examined using a two pulse protocol. Data were analyzed and fitted using OriginPro v.7.5 (OriginLab, Northampton, Mass.) software. Table 3 shows data obtained according to these methods.

TABLE 3

| Compound | $V_{1/2}$ fast inactivation (mV) | $V_{1/2}$ slow inactivation (mV) | Fraction current remaining at −40 mV | τ recovery from fast inactivation (ms) | τ recovery from slow inactivation (ms) | Fraction of current recovered at 5.1 s interval |
|---|---|---|---|---|---|---|
| Control ECS | −61 | −75 | 0.62 | 270 | 533 | 0.96 |
| 3 | −64 | −78 | *0.40 | *512 | *903 | 0.91 |
| 4 | — | — | — | — | 495 | 0.98 |

$V_{1/2}$: voltage-dependence of half inactivation
*P < 0.005

Example 6

$Na_v1.5/1.7/1.8$ Voltage-Clamp Electrophysiological Assays

To examine the effects of compounds on enhancement of slow inactivation of $Na_v1.7$ and $Na_v1.8$ channels expressed in HEK cells the culture media was replaced with an extracellular solution containing (in mM): 137 NaCl, 4 KCl, 1.8 $CaCl_2$, 1 $MgCl_2$, 10 HEPES, 10 glucose, pH adjusted to 7.4 with NaOH. The intracellular solution contained (in mM): 130 KCl, 1 $MgCl_2$, 5 EGTA, 10 HEPES, 5 $K_2ATP$, adjusted to pH 7.3 with KOH. Whole-cell recordings, preparation and application of test compounds were performed in a similar manner to the $Ca_v3.2$ electrophysiological assays. Voltage protocols were applied to quantify the effects of test compounds to enhance slow inactivation for $Na_v1.7$ and $Na_v1.8$. Table 4 shows data obtained for Compound 9 in the $Na_v1.7$ assay.

TABLE 4

| Compound | Concentration tested | Fraction current remaining | n cells |
|---|---|---|---|
| 9 | 10 μM | 0.93 | 5 |
|   | 100 μM | 0.86 | 5 |

Inhibition of the TTX-resistant $Na_v1.5$ sodium channel, a key cardiac ion channel, can have profound effects on the duration and amplitude of the cardiac action potential and can result in arrhythmias and other heart malfunctions. To assess the potential cardiac liability of compounds at an early stage in the drug discovery process, a $Na_v1.5$ sodium channel screening assay is performed on Molecular Device's PatchXpress™ automated electrophysiology platform. Under voltage-calmp conditions, $Na_v1.5$ currents are recorded from HEK cells expressing the human Nav1.5 channel in the absence and presence of increasing concentrations of the test compound to obtain an $IC_{50}$ value. The external recording solution contained (in mM): 90 TEACl, 50 NaCl, 1.8 CaCl, 1 $MgCl_2$, 10 HEPES, 10 glucose, adjusted to pH 7.4 with TEA-OH and to 300 mOsm with sucrose (if necessary), while the internal patch pipette solution contained (in mM): 129 CsF, 2 $MgCl_2$, 11 EGTA, 10 HEPES, 3 $Na_2ATP$ adjusted to pH 7.2 with CsOH and to 290 mOsm with sucrose (if necessary). $Na_v1.5$ channel currents were evoked using a cardiac action potential waveform at 1 Hz, digitized at 31.25 kHz and low-pass filtered at 12 kHz. As shown in Table 5, Compound 4 did not act as inhibitors of the cardiac $Na_v$ 1.5 channel.

TABLE 5

| Compound no. | $HNA_V 1.5$ CARDIAC AP 1 Hz $IC_{50}$ |
|---|---|
| 4 | 300000 |

Example 7

L5/L6 Spinal Nerve Ligation (SNL)—Chung Pain Model

The Spinal Nerve Ligation is an animal model representing peripheral nerve injury generating a neuropathic pain syndrome. In this model experimental animals develop the clinical symptoms of tactile allodynia and hyperalgesia. L5/L6 Spinal nerve ligation (SNL) injury was induced using the procedure of Kim and Chung (Kim et al., *Pain* 50:355-363 (1992)) in male Sprague-Dawley rats (Harlan; Indianapolis, Ind.) weighing 200 to 250 grams.

Anaesthesia was induced with 2% isofluorane in $O_2$ at 2 L/min and maintained with 0.5% isofluorane in $O_2$. Rats were then shaved and aseptically prepared for surgeries. A 2 cm paraspinal incision was made at the level of L4-S2. L4/L5 was exposed by removing the transverse process above the nerves with a small rongeur. The L5 spinal nerve is the larger of the two visible nerves below the transverse process and lies closest to the spine. The L6 spinal nerve is located beneath the corner of the slope bone. A home-made glass Chung rod was used to hook L5 or L6 and a pre-made slip knot of 4.0 silk suture was placed on the tip of the rod just above the nerve and pulled underneath to allow for the tight ligation. The L5 and L6 spinal nerves were tightly ligated distal to the dorsal root ganglion. The incision was closed, and the animals were allowed to recover for 5 days. Rats that exhibited motor deficiency (such as paw-dragging) or failure to exhibit subsequent tactile allodynia were excluded from further testing.

Sham control rats underwent the same operation and handling as the experimental animals, but without SNL.

Prior to initiating drug delivery, baseline behavioural testing data is obtained. At selected times after infusion of the Test or Control Article behavioural data can then be collected again.

A. Assessment of Tactile Allodynia—Von Frey

The assessment of tactile allodynia consisted of measuring the withdrawal threshold of the paw ipsilateral to the site of nerve injury in response to probing with a series of calibrated von Frey filaments (innocuous stimuli). Animals were acclimated to the suspended wire-mesh cages for 30 min before testing. Each von Frey filament was applied perpendicularly to the plantar surface of the ligated paw of rats for 5 sec. A positive response was indicated by a sharp withdrawal of the paw. For rats, the first testing filament is 4.31. Measurements were taken before and after administration of test articles. The paw withdrawal threshold was determined by the non-parametric method of Dixon (Dixon, *Ann. Rev. Pharmacol. Toxicol.* 20:441-462 (1980)), in which the stimulus was incrementally increased until a positive response was obtained, and then decreased until a negative result was observed. The protocol was repeated until three changes in behaviour were determined ("up and down" method) (Chaplan et al., *J. Neurosci. Methods* 53:55-63 (1994)). The 50% paw withdrawal threshold was determined as $(10^{[Xf+k\delta]})/10,000$, where $X_f$=the value of the last von Frey filament employed, k=Dixon value for the positive/negative pattern, and $\delta$=the logarithmic difference between stimuli. The cut-off values for rats were no less than 0.2 g and no higher than 15 g (5.18 filament); for mice no less than 0.03 g and no higher than 2.34 g (4.56 filament). A significant drop of the paw withdrawal threshold compared to the pre-treatment baseline is considered tactile allodynia.

Rat SNL tactile allodynia were tested for Compounds 1-4 and 9-12 at 60 minutes compared to baseline and post-SNL. Compounds 1, 9, and 13 showed significant anti-allodynia as shown in FIG. 1 and in Table 6 below. Compound 4 showed significant antiallodynia (FIG. 1). FIG. 1 is a plot of the antiallodynic effects of compound 4 (i.p.) tested in SNL L5/L6 rats using von Frey at three different doses, namely 3, 10 and 30 mpk, compared to vehicle alone. The "*" indication in the plot indicates statistically significant antiallodynic effects of compound 4 compared to the vehicle at 60 minutes after drug administration at all three doses. Rat SNL tactile allodynia were tested at 1, 2 and 4 hours after drug treatment (Table 6).

TABLE 6

| Compound | Rat SNL Tactile Allodynia (% Antiallodynia) | | |
|---|---|---|---|
| no. | 1 hour | 2 hours | 4 hours |
| 1 | 10 | 19 | 26 |
| 3 | 51 | 49 | 30 |
| 4 | 92 | — | — |
| 7 | 10 | 9 | 14 |
| 8 | 17 | 24 | 17 |
| 9 | 7 | 10 | 7 |
| 15 | 11 | 8 | 15 |

B. Assessment of Thermal Hypersensitivity—Hargreaves

The method of Hargreaves and colleagues (Hargreaves et al., *Pain* 32:77-8 (1988)) can be employed to assess paw-withdrawal latency to a noxious thermal stimulus.

Rats may be allowed to acclimate within a Plexiglas enclosure on a clear glass plate for 30 minutes. A radiant heat source (e.g., halogen bulb coupled to an infrared filter) can then be activated with a timer and focused onto the plantar surface of the affected paw of treated rats. Paw-withdrawal latency can be determined by a photocell that halts both lamp and timer when the paw is withdrawn. The latency to withdrawal of the paw from the radiant heat source can be determined prior to L5/L6 SNL, 7-14 days after L5/L6 SNL but before drug, as well as after drug administration. A maximal cut-off of 33 seconds is typically employed to prevent tissue damage. Paw withdrawal latency can be thus determined to the nearest 0.1 second. A significant drop of the paw withdrawal latency from the baseline indicates the status of thermal hyperalgesia. Antinociception is indicated by a reversal of thermal hyperalgesia to the pre-treatment baseline or a significant (p<0.05) increase in paw withdrawal latency above this baseline. Data is converted to % anti hyperalgesia or % anti nociception by the formula: (100×(test latency−baseline latency)/(cut-off−baseline latency) where cut-off is 21 seconds for determining anti hyperalgesia and 40 seconds for determining antinociception.

Example 8

6 Hz Psychomotor Seizure Model of Partial Epilepsy

Compounds were evaluated for the protection against seizures induced by a 6 Hz, 0.2 ms rectangular pulse width of 3 s duration, at a stimulus intensity of 32 mA (CC97) applied to the cornea of male CF1 mice (20-30 g) according to procedures described by Barton et al, "Pharmacological Characterization of the 6 Hz Psychomotor Seizure Model of Partial Epilepsy," *Epilepsy Res.* 47(3):217-27 (2001). Seizures are characterised by the expression of one or more of the following behaviours: stun, forelimb clonus, twitching of the vibrissae and Straub-tail immediately following electrical stimulation. Animals were considered "protected" if following pre-treatment with a compound the 6 Hz stimulus failed to evoke a behavioural response as describe above. Exemplary results using this assay are shown in Table 7.

TABLE 7

| | Epilepsy 6 Hz (% Protected) | | | | | Epilepsy |
|---|---|---|---|---|---|---|
| Compound No. | 0.25 hour | 0.5 hour | 1 hour | 2 hours | 4 hours | 6 Hz $ED_{50}$ |
| 3 | 0 | 0 | 0 | 0 | 0 | — |
| 4 | 50 | 88 | 13 | 25 | — | 192 |

Example 9

GAERS (Genetic Absence Epilepsy Rats from Strasbourg) Epilepsy Model

The GAERS (Genetic Absence Epilepsy Rats from Strasbourg) is noted for its long and frequently recurring absence seizure episodes. Investigators have determined, using electrophysiological recordings from neurons within the thalamus, that the activity and expression of the low-voltage calcium channels is significantly increased in GAERS. Eight female GAERS rats, bred in the Ludwig Institute for Cancer Research, were used for this study. Rats weighed between 180 and 250 g and aged between 18 and 26 weeks at the start of the experiment.

Electrodes can be made by soldering together gold-plated sockets (220-S02 Ginder Scientific, VA, Canada), stainless steel teflon coated wire (SDR clinical technology, NSW, Australia) and a small stainless steel screw (1.4×3 mm, Mr. Specks, Australia). Animals can be anaethetised with inhalation of Isoflurane in equal parts of medical air and oxygen (5% induction, 2.5-1.5% maintenance) or alternatively by intraperitoneal injection with xylazine (10 mg/kg) and ketamine (75 mg/kg). The animals can be fixated in a stereotaxic frame by means of ear bars. A midline incision on the scalp was made, skin and connective tissue is scraped and pushed laterally to expose underlying skull. Six holes are drilled bilaterally, two in the frontal bone and four in the parietal bone, approximately 2 mm anterior to bregma, and four and 10 mm posterior to bregma. Six electrodes are then implanted in the holes, and gold-plated sockets were clipped into 9-pin ABS plug (GS09PLG-220, Ginder Scientific, Canada). Two side-anchoring screws can be placed laterally into skull to improve strength of cap fixation. Caps can then be held in place with dental cement.

Post-operatively, animals are given the analgesic Rimadyl (4 mg/kg), placed in their cages on a heat mat, and observed until recovery. Rats are caged separately throughout the study, weighed and health-checked daily, and are allowed 7 days to recover prior to commencement of the experimental procedures. Rats are typically allowed free access to rodent chow (brand, WA stock feeders) and water under 12:12 light dark conditions in the Biological Research Facility of the Department of Medicine (RMH).

Prior to first drug treatment, rats are tested for absence-type seizures, which are accompanied by generalised spike and wave discharges (SWD) on an EEG recording. Testing, and all further experiments are performed in a quiet, well lit room with rats in their home cages. Rats are connected via 6-channel wire cables, which are cut and soldered to six gold-plated pins inserted into a 9 pin socket. Cables can be connected to a computer running Compumedics™ EEG acquisition software (Melbourne, Australia). Three rats that do not have adequate baseline seizures at the start of the study can be commenced in week 2 and their treatments can be made up for at the end according to the schedule. On week 1, day 1, after the acclamation period following surgical implantation of subdural electrodes, four animals can be habituated with the cable connected for 15 minutes, and then have their SWDs recorded for 60 minutes as baseline. Immediately following baseline, rats are given one of the test, reference, or control articles according to the treatment schedule, and target period is recorded from 15 minutes after injection for 120 minutes. Animals are monitored throughout the experiment, and are kept quietly wakeful during baseline and target periods.

The seizure expression for the 60 minutes pre-injection and 120 minutes post-injection EEG recording (starting 15 minutes post-drug administration) are quantified by marking the start and finish of the burst of SWDs. This can be done with the assistance of SWCFinder® software which has been custom designed to quantitate GAERS seizures, and researchers are blinded to the nature of the drug administered, whereby the analysis is performed blinded. Standard criteria for GAERS seizures is an SWD burst of amplitude of more than three times baseline, a frequency of 7 to 12 Hz, and a duration of longer than 0.5 s. From this, the total percent time spent in seizure over the 120 minutes post-injection EEG recording can be determined (percentage time in seizure) as the primary outcome variable.

Example 10

Mouse Rotarod Assay

To assess a compound's undesirable side effects (toxicity), animals were monitored for overt signs of impaired neurological or muscular function. In mice, the rotarod procedure (Dunham and Miya, *J. Am. Pharmacol. Assoc.* 46:208-209 (1957)) is used to disclose minimal muscular or neurological impairment (MMI). When a mouse is placed on a rod that rotates at a speed of 6 rpm, the animal can maintain its equilibrium for long periods of time. The animal is considered toxic if it falls off this rotating rod three times during a 1-mM period. In addition to MMI, animals may exhibit a circular or zigzag gait, abnormal body posture and spread of the legs, tremors, hyperactivity, lack of exploratory behavior, somnolence, stupor, catalepsy, loss of placing response and changes in muscle tone. Exemplary data obtained using this assay are shown in Table 8.

TABLE 8

| Compound no. | % Impaired | | | | | |
|---|---|---|---|---|---|---|
| | 0.25 hr | 0.5 hr | 1 hr | 2 hr | 4 hr | $TD_{50}$ |
| 3 | 0 | 0 | 0 | 0 | 0 | — |
| 4 | 0 | 0 | 0 | 0 | 0 | 370 |

Example 11

Lamina Assay and Data

Recordings on Lamina I/II Spinal Cord Neurons.

Male Wistar rats (P6 to P9 for voltage-clamp and P15 to P18 for current-clamp recordings) were anaesthetized through intraperitoneal injection of Inactin (Sigma). The spinal cord was then rapidly dissected out and placed in an ice-cold solution protective sucrose solution containing (in mM): 50 sucrose, 92 NaCl, 15 D-Glucose, 26 $NaHCO_3$, 5 KCl, 1.25 $NaH_2PO_4$, 0.5 $CaCl_2$, 7 $MgSO_4$, 1 kynurenic acid, and bubbled with 5% $CO_2$/95% $O_2$. The meninges, dura, and dorsal and ventral roots were then removed from the lumbar region of the spinal cord under a dissecting microscope. The "cleaned" lumbar region of the spinal cord was glued to the vibratome stage and immediately immersed in ice cold, bubbled, sucrose solution. For current-clamp recordings, 300 to 350 µm parasagittal slices were cut to preserve the dendritic arbour of lamina I neurons, while 350 to 400 µm transverse slices were prepared for voltage-clamped $Na_v$ channel recordings. Slices were allowed to recover for 1 hour at 35° C. in Ringer solution containing (in mM): 125 NaCl, 20 D-Glucose, 26 $NaHCO_3$, 3 KCl, 1.25 $NaH_2PO_4$, 2 $CaCl_2$, 1 $MgCl_2$, 1 kynurenic acid, 0.1 picrotoxin, bubbled with 5% $CO_2$/95%

O₂. The slice recovery chamber was then returned to room temperature (20 to 22° C.) and all recordings were performed at this temperature.

Neurons were visualized using IR-DIC optics (Zeiss Axioskop 2 FS plus, Gottingen, Germany), and neurons from lamina I and the outer layer of lamina II were selected based on their location relative to the substantia gelatinosa layer. Neurons were patch-clamped using borosilicate glass patch pipettes with resistances of 3 to 6 MΩ. Current-clamp recordings of lamina I/II neurons in the intact slice, the external recording solution was the above Ringer solution, while the internal patch pipette solution contained (in mM): 140 KGluconate, 4 NaCl, 10 HEPES, 1 EGTA, 0.5 MgCl₂, 4 MgATP, 0.5 Na₂GTP, adjusted to pH 7.2 with 5 M KOH and to 290 mOsm with D-Mannitol (if necessary). Only tonic firing neurons were selected for current-clamp experiments, while phasic, delayed onset and single spike neurons were discarded (22). Recordings were digitized at 50 kHz and low-pass filtered at 2.4 kHz.

Data obtained according to this protocol for compounds 3 and 4 are shown in Table 9.

TABLE 9

| | LAMINA I AND II | | | |
|---|---|---|---|---|
| Compound no. | % Spike Change (Mean; % change from control) | % Spike Change SEM | % Spike Change P < 0.05 | EC$_{50}$ |
| 3 | 28.7 | 8.6 | no | — |
| 4 | −5.3 | 8.8 | No | 370 |

Example 12

Pharmacokinetic Parameters

Preliminary exposure characteristics of the compounds were evaluated in an in vivo Rat Early Pharmacokinetic (EPK) study design (Table 10), and the data show that the compounds are orally bioavailable. Male Sprague-Dawley rats were dosed via oral (PO) gavage in the detailed formulation. Blood samples were collected from the animals at 6 timepoints out to 4 hours post-dose. Pharmacokinetic analysis was performed on the LC-MS/MS measured concentrations for each timepoint of each compound.

TABLE 10

| Compound No. | Dose (mg/kg) | Route | Formulation | Dose Normalized Cmax (nM) | Dose Normalized AUC (nM * h) | $T_{max}$ (hr) |
|---|---|---|---|---|---|---|
| 1 | 30 | PO | 0.5% CMC | 333 | 993 | 1.7 |
| 2 | 30 | PO | 0.5% CMC | 182 | 283 | 0.5 |
| 4 | 3 | PO | PG | 832 | 522 | 0.25 |
| 7 | 30 | PO | 0.5% CMC | 730 | 1087 | 0.5 |
| 8 | 30 | PO | 0.5% CMC | 132 | 185 | 0.67 |

PG: Propylene glycol
CMC: 0.5% Carboxy methyl cellulose

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications, patents and patent applications are herein incorporated by reference in their entirety to the same extent as if each individual publication, patent or patent application was specifically and individually indicated to be incorporated by reference in its entirety.

What is claimed is:

1. A compound of the formula:

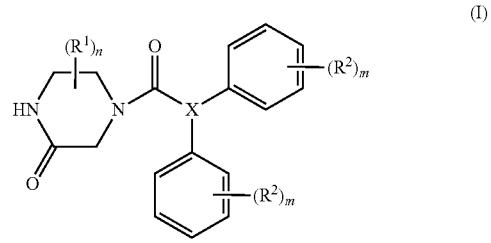

(I)

or a pharmaceutically acceptable salt thereof, or a stereoisomer thereof, wherein X is an optionally substituted alkylene (1-6C), alkenylene (2-6C), alkynylene (2-6C), heteroalkylene (2-6C), heteroalkenylene (2-6C), or heteroalkynylene (2-6C);

n is 1 or 2;

each m is, independently, an integer between 0-5;

each R¹ is methyl; and each R² is, independently, selected from halo, CN, NO₂, CF₃, OCF₃, COOR', CONR'₂, OR', SR', SOR', SO₂R', NR'₂, NR'(CO)R', and NR'SO₂R', wherein each R' is independently H or an optionally substituted group selected from alkyl (1-6C), alkenyl (2-6C), alkynyl (2-6C), heteroalkyl (2-6C) heteroalkenyl (2-6), and heteroalkynyl (2-6C); or each R² is an optionally substituted group selected from alkyl (1-6C), alkenyl (2-6C), alkynyl (2-6C), heteroalkyl (2-6C), heteroalkenyl (2-6C), or heteroalkynyl (2-6C).

2. A compound of the formula:

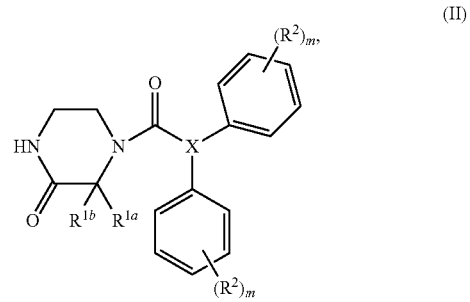

(II)

or a pharmaceutically acceptable salt thereof, or a stereoisomer thereof, wherein both $R^{1a}$ and $R^{1b}$ are unsubstituted 1C-6C alkyl;

X is CH, CH₂CH, (CH₂)₂₋₄CH, CH═C, NHCH, or CH₂S(═O)CH;

each m is, independently, 0, 1, or 2; and each R² is, independently, optionally substituted 1C-6C alkyl or halogen.

3. The compound of claim 2, wherein both $R^{1a}$ and $R^{1b}$ are methyl.

4. A compound of the formula:

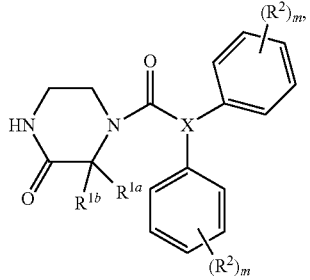
(II)

or a pharmaceutically acceptable salt thereof, or a stereoisomer thereof, wherein
- $R^{1a}$ is H and $R^{1b}$ is unsubstituted 1C-6C alkyl;
- X is CH, $CH_2CH$, $(CH_2)_{2-4}CH$, CH=C, NHCH, or $CH_2S(=O)CH$;
- each m is, independently, 0, 1, or 2; and
- each $R^2$ is, independently, optionally substituted 1C-6C alkyl or halogen.

5. The compound of claim 4, wherein said unsubstituted 1C-6C alkyl is methyl.

6. The compound of claim 4, wherein the carbon to which $R^{1a}$ and $R^{1b}$ are bonded has the R configuration.

7. The compound of claim 4, wherein the carbon to which $R^{1a}$ and $R^{1b}$ are bonded has the S configuration.

8. A compound of the formula:

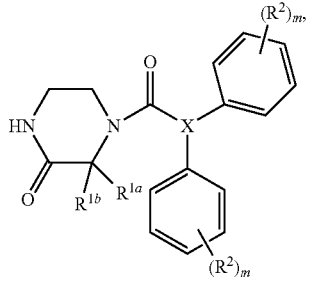
(II)

or a pharmaceutically acceptable salt thereof, or a stereoisomer thereof, wherein
- each $R^{1a}$ and $R^{1b}$ is selected, independently, from H or unsubstituted 1C-6C alkyl;
- X is CH, $CH_2CH$, $(CH_2)_{2-4}CH$, CH=C, NHCH, or $CH_2S(=O)CH$;
- each m is 1; and
- each $R^2$ is, independently, optionally substituted 1C-6C alkyl or halogen, and
- wherein both $R^2$ are ortho to X, or
- wherein both $R^2$ are meta to X.

9. The compound of claim 8, wherein both $R^2$ are meta to X.

10. The compound of claim 8, wherein both $R^2$ are ortho to X.

11. A compound of the formula, wherein said compound has a structure according to

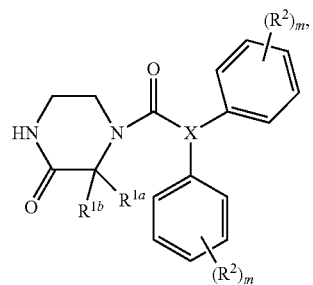
(II)

or a pharmaceutically acceptable salt thereof, or a stereoisomer thereof, wherein
- each $R^{1a}$ and $R^{1b}$ is selected, independently, from H or unsubstituted 1C-6C alkyl;
- X is CH, $CH_2CH$, $(CH_2)_{2-4}CH$, CH=C, NHCH, or $CH_2S(=O)CH$;
- each m is, independently, 0, 1, or 2; and
- each $R^2$ is selected, independently, from chloro or methyl.

12. A compound selected from the group consisting of:
- N-benzhydryl-3-oxopiperazine-1-carboxamide;
- 4-(2-(benzhydrylsulfinyl)acetyl)piperazin-2-one;
- 4-(3,3-bis(4-chlorophenyl)propanoyl)piperazin-2-one;
- 4-(3,3-di-tolylpropanoyl)piperazin-2-one;
- 4-(6,6-diphenylhexanoyl)piperazin-2-one;
- 4-(2,2-diphenylacetyl)piperazin-2-one;
- 4-(3,3-diphenylacryloyl)piperazin-2-one;
- 4-(3,3-bis(4-fluorophenyl)propanoyl)piperazin-2-one;
- 4-(3,3-diphenylpropanoyl)-3,3-dimethylpiperazin-2-one;
- (R)-4-(3,3-diphenylpropanoyl)-3-methylpiperazin-2-one;
- (S)-4-(3,3-diphenylpropanoyl)-3-methylpiperazin-2-one;
- 4-(2,2-bis(4-chlorophenyl)acetyl)piperazin-2-one;
- 4-(2-(diphenylamino)acetyl)piperazin-2-one; and
- 4-(3,3-bis(4-fluorophenyl)propanoyl)-3,3-dimethylpiperazin-2-one;

or a pharmaceutically acceptable salt thereof, or a stereoisomer thereof.

13. The compound of claim 12, wherein said compound is:

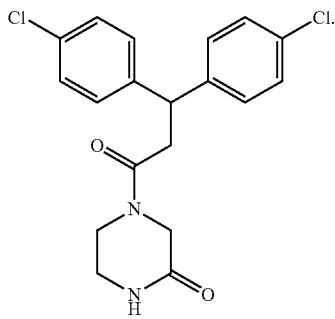 [SMILES: O=C1CN(C(=O)CC(c2ccc(Cl)cc2)c2ccc(Cl)cc2)CCN1]

14. A pharmaceutical composition comprising a pharmaceutically acceptable excipient and
(a) the compound of claim 1; or
(b) a compound according to formula (III),

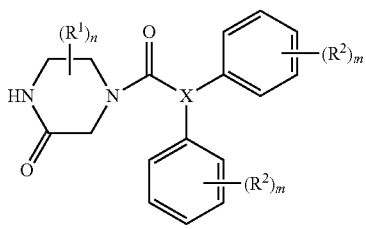

(III)

or a pharmaceutically acceptable salt, solvate, or prodrug thereof, or a stereoisomer thereof, or a conjugate thereof, wherein X is an optionally substituted alkylene (1-6C), alkenylene (2-6C), alkynylene (2-6C), heteroalkylene (2-6C), heteroalkenylene (2-6C), or heteroalkynylene (2-6C);

n is an integer between 0-6;

each m is, independently, an integer between 0-5;

each $R^1$ and $R^2$ is independently selected from halo, CN, $NO_2$, $CF_3$, $OCF_3$, COOR', CONR'$_2$, OR', SR', SOR', $SO_2R'$, NR'$_2$, NR'(CO)R', and NR'$SO_2R'$, wherein each R' is independently H or an optionally substituted group selected from alkyl (1-6C), alkenyl (2-6C), alkynyl (2-6C), heteroalkyl (2-6C) heteroalkenyl (2-6), and heteroalkynyl (2-6C); or the optional substituents may be one or more optionally substituted groups selected from alkyl (1-6C), alkenyl (2-6C), alkynyl (2-6C), heteroalkyl (2-6C), heteroalkenyl (2-6C), or heteroalkynyl (2-6C); and wherein each $R^1$ may further be selected from =O and =NOR'.

15. The pharmaceutical composition of claim 14, wherein said pharmaceutical composition is formulated in unit dosage form.

16. The pharmaceutical composition of claim 15, wherein said unit dosage form is a tablet, caplet, capsule, lozenge, film, strip, gelcap, or syrup.

17. A pharmaceutical composition comprising a pharmaceutically acceptable excipient and the compound of claim 12.

18. The pharmaceutical composition of claim 17, wherein said pharmaceutical composition is formulated in unit dosage form.

19. The pharmaceutical composition of claim 18, wherein said unit dosage form is a tablet, caplet, capsule, lozenge, film, strip, gelcap, or syrup.

20. A pharmaceutical composition comprising a pharmaceutically acceptable excipient and the compound of claim 13.

21. The pharmaceutical composition of claim 20, wherein said pharmaceutical composition is formulated in unit dosage form.

22. The pharmaceutical composition of claim 21, wherein said unit dosage form is a tablet, caplet, capsule, lozenge, film, strip, gelcap, or syrup.

\* \* \* \* \*